(12) United States Patent
Edwards et al.

(10) Patent No.: US 10,526,363 B2
(45) Date of Patent: Jan. 7, 2020

(54) SUBSTITUTED PHOSPHORAMIDATE COMPOUNDS AND USES THEREOF

(71) Applicants: Merck Sharp & Dohme Corp., Rahway, NJ (US); Merck Sharp & Dohme Limited, Hoddesdon, Hertfordshire (GB); John Simon Edwards, Hertfordshire (GB); Peter Richard Mullens, Hertfordshire (GB); Edward Cleator, Whittlesford (GB); Bryon L. Simmons, Hamilton, NJ (US); Courtney K. Maguire, Piscataway, NJ (US); Jeremy Peter Scott, Hertfordshire (GB); Nobuyoshi Yasuda, Mountainside, NJ (US); Yong-Li Zhong, Edison, NJ (US); Lisa F. Frey, Somerset, NJ (US); Peter G. Dormer, Westfield, NJ (US); Andrew Brunskill, Watchung, NJ (US); Artis Klapars, Edison, NJ (US); Pu Qian, Shanghai (CN); Yi Zhang, Shanghai (CN); Baoqiang Wan, Shanghai (CN); Eric Ashley, Fanwood, NJ (US)

(72) Inventors: John Simon Edwards, Hertfordshire (GB); Peter Richard Mullens, Hertfordshire (GB); Edward Cleator, Whittlesford (GB); Bryon L. Simmons, Hamilton, NJ (US); Courtney K. Maguire, Piscataway, NJ (US); Jeremy Peter Scott, Hertfordshire (GB); Nobuyoshi Yasuda, Mountainside, NJ (US); Yong-Li Zhong, Edison, NJ (US); Lisa F. Frey, Somerset, NJ (US); Peter G. Dormer, Westfield, NJ (US); Andrew Brunskill, Watchung, NJ (US); Artis Klapars, Edison, NJ (US); Pu Qian, Shanghai (CN); Yi Zhang, Shanghai (CN); Baoqiang Wan, Shanghai (CN); Eric Ashley, Fanwood, NJ (US)

(73) Assignees: Merck Sharp & Dohme Corp., Rahway, NJ (US); Merck Sharp & Dohme Ltd., Hertfordshire (GB)

( * ) Notice: Subject to any disclaimer, the term of this patent is extended or adjusted under 35 U.S.C. 154(b) by 0 days.

(21) Appl. No.: 15/503,776

(22) PCT Filed: Aug. 14, 2015

(86) PCT No.: PCT/CN2015/087061
§ 371 (c)(1),
(2) Date: Feb. 14, 2017

(87) PCT Pub. No.: WO2016/023522
PCT Pub. Date: Feb. 18, 2016

(65) Prior Publication Data
US 2017/0275327 A1    Sep. 28, 2017

Related U.S. Application Data

(60) Provisional application No. 62/037,756, filed on Aug. 15, 2014.

(51) Int. Cl.
*C07H 19/10* (2006.01)
*C07F 9/58* (2006.01)
(Continued)

(52) U.S. Cl.
CPC ............. *C07H 19/10* (2013.01); *C07F 9/242* (2013.01); *C07F 9/2458* (2013.01);
(Continued)

(58) Field of Classification Search
None
See application file for complete search history.

(56) References Cited

U.S. PATENT DOCUMENTS

| 7,879,815 B2 | 2/2011 | MacCoss et al. |
| 8,629,263 B2 | 1/2014 | Ross et al. |

(Continued)

FOREIGN PATENT DOCUMENTS

| CN | 101918425 | 12/2010 |
| CN | 104031104 A | 9/2014 |

(Continued)

OTHER PUBLICATIONS

Hamon, N., Quintiliani, M., Balzarini, J., & McGuigan, C. (2013). Synthesis and biological evaluation of prodrugs of 2-fluoro-2-deoxyribose-1-phosphate and 2, 2-difluoro-2-deoxyribose-1-phosphate. Bioorganic & medicinal chemistry letters, 23(9), 2555-2559. (Year: 2013).*

(Continued)

*Primary Examiner* — Dale R Miller
(74) *Attorney, Agent, or Firm* — Jeffrey P. Bergman; Catherine D. Fitch

(57) ABSTRACT

The present invention is directed to Compounds of Formula (I) and salts thereof, wherein $R^1$, $R^2$, $R^3$ and $R^4$ are defined above herein. The present invention is also directed to uses of the compounds of Formula (I) to add phosphoramidate groups onto organic alcohols.

(I)

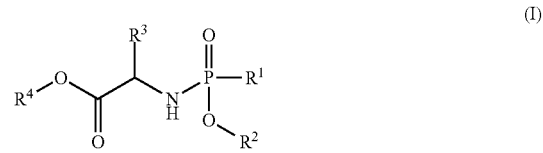

8 Claims, No Drawings

(51) Int. Cl.
*C07H 19/06* (2006.01)
*C07F 9/24* (2006.01)
*C07F 9/6558* (2006.01)

(52) U.S. Cl.
CPC .............. *C07F 9/2487* (2013.01); *C07F 9/58* (2013.01); *C07F 9/65586* (2013.01); *C07H 19/06* (2013.01)

(56) References Cited

U.S. PATENT DOCUMENTS

| | | |
|---|---|---|
| 2011/0251152 A1 | 10/2011 | Ross et al. |
| 2014/0309413 A1 | 10/2014 | Rose et al. |
| 2015/0361123 A1 | 12/2015 | Wang et al. |

FOREIGN PATENT DOCUMENTS

| | | | | |
|---|---|---|---|---|
| WO | WO2005003147 | | 1/2005 | |
| WO | 2008121634 A1 | | 9/2008 | |
| WO | WO2009132123 | | 10/2009 | |
| WO | 20100002877 | | 1/2010 | |
| WO | 2010081628 | | 7/2010 | |
| WO | WO2010075517 | | 7/2010 | |
| WO | WO2011035231 | | 3/2011 | |
| WO | 2014169280 A2 | | 10/2014 | |
| WO | WO-2014169278 A1 | * | 10/2014 | ......... A61K 31/4709 |
| WO | 2016016865 A1 | | 2/2016 | |

OTHER PUBLICATIONS

Serpi, M., Bibbo, R., Rat, S., Roberts, H., Hughes, C., Caterson, B., . . . & McGuigan, C. (2012). Novel phosphoramidate prodrugs of N-acetyl-(D)-glucosamine with antidegenerative activity on bovine and human cartilage explants. Journal of medicinal chemistry, 55(10), 4629-4639. (Year: 2012).*
Sosnovsky, G., & Konieczny, M. (1976). Phosphorylative spin-labeling of amino acids and steroids. Synthesis, 1976(08), 537-539. (Year: 1976).*
Bobeck et al., Advances in nucleoside monophosphate prodrugs as anti-HCV agents, Antiviral Therapy, 2010, 935-950, 15.
International Search Report and Written Opinion for PCT/CN2015/087061, dated May 13, 2016, 16 pages.
McGuigan et al., Design, synthesis and evaluation of a novel double pro-drug: INX-08189. A new clinical candidate for hepatitis C virus, Bioorganic & Medicinal Chemistry Letters, 2010, pp. 4850-4854, 20(16).

* cited by examiner

SUBSTITUTED PHOSPHORAMIDATE COMPOUNDS AND USES THEREOF

CROSS-REFERENCE TO RELATED APPLICATIONS

This application is the national stage application under 35 U.S.C. 371 of International Patent Application No. PCT/CN15/0087061, filed Aug. 14, 2015, which claims priority to U.S. Provisional Patent Application No. 62/037,756, filed Aug. 15, 2014. Each of the aforementioned PCT and provisional applications is incorporated by reference in its entirety.

FIELD OF THE INVENTION

The present invention is directed to Substituted Phosphoramidate Compounds and to uses of the Substituted Phosphoramidate Compounds to add phosphoramidate groups onto organic alcohols.

BACKGROUND OF THE INVENTION

Hepatitis C virus (HCV) infection is a major health problem that leads to chronic liver disease, such as cirrhosis and hepatocellular carcinoma, in a substantial number of infected individuals, estimated to be 2-15% of the world's population.

The development of inhibitors of HCV NS5B polymerase with potential for the treatment of HCV infection has been reviewed in Poordad et al. (2012), supra; Asselah et al. (2009), supra; and Chatel-Chaix et al. Direct-acting and host-targeting HCV inhibitors: current and future directions. *Current Opinion in Virology*, 2:588-598 (2012). Nucleoside analogs that inhibit HCV NS5B polymerase are disclosed, for example, in WO 2011/035231, WO 2005/003147, WO 2010/0081628, U.S. Pat. No. 7,879,815, WO 2010/075517, WO 2010/002877, and WO 2009/132123.

Among these nucleoside analogs are prodrugs which have the 5'-OH group masked as a phosphoramidate moiety (also referred to as "McGuigan" prodrugs). See, for example, Bobeck et al., *Antiviral Therapy*, 15:935-950 (2010); and McGuigan et al., *Bioorg Med Chem Lett*, 20(16)4850-4854 (2010). U.S. Pat. No. 8,629,263 discloses reagents that can be used to add phosphoramidate groups onto nucleoside compounds to prepare McGuigan type prodrugs.

SUMMARY OF THE INVENTION

The present invention is directed to Compounds of Formula (I) (the "Substituted Phosphoramidate Compounds")

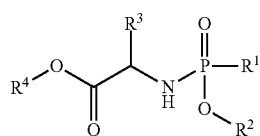

(I)

wherein:
R$^1$ is selected from 5 or 6-membered monocyclic heteroaryl, 9 or 10-membered bicyclic heteroaryl, —O-(5 or 6-membered monocyclic heteroaryl), —O-(9 or 10-membered bicyclic heteroaryl), —O-(4 to 7-membered monocyclic heterocycloalkyl), —S-(5 or 6-membered monocyclic heteroaryl), —S-(9 or 10-membered bicyclic heteroaryl), —S-(4 to 7-membered monocyclic heterocycloalkyl) or 9 or 10-membered bicyclic heteroaryl) and —S—($C_6$-$C_{10}$ aryl), wherein any of said 5 or 6-membered monocyclic heteroaryl groups, any of said 9 or 10-membered bicyclic heteroaryl groups, any of said 4 to 7-membered monocyclic heterocycloalkyl groups, and said $C_6$-$C_{10}$ aryl group can each be optionally substituted with one or more R$^5$ groups;

R$^2$ is selected from $C_6$-$C_{10}$ aryl, 5 or 6-membered monocyclic heteroaryl and 9 or 10-membered bicyclic heteroaryl, wherein said $C_6$-$C_{10}$ aryl group, said 5 or 6-membered monocyclic heteroaryl group and said 9 or 10-membered bicyclic heteroaryl group can be optionally substituted with one or more R$^5$ groups;

R$^3$ is selected from $C_1$-$C_6$ alkyl, $C_3$-$C_7$ cycloalkyl, phenyl or benzyl, wherein said $C_3$-$C_7$ cycloalkyl group, said phenyl group and the phenyl moiety of said benzyl group can be optionally substituted with one or more R$^5$ groups;

R$^4$ is selected from $C_1$-$C_6$ alkyl, $C_2$-$C_6$ alkenyl, —($C_1$-$C_3$ alkylene)$_m$-($C_3$-$C_{14}$ cycloalkyl) and —($C_1$-$C_3$ alkylene)$_m$-($C_6$-$C_{10}$ aryl);

each occurrence of R$^5$ is independently selected from —$C_1$-$C_6$ alkyl, halo, —OR$^6$, —C(O)R$^6$, —CO$_2$R$^6$, —SR$^6$, —$C_1$-$C_6$ hydroxyalkyl, —$C_1$-$C_6$ haloalkyl, —N(R$^6$)$_2$, —S(O)R$^6$, —S(O)$_2$R$^6$, —CN and —NO$_2$;

each occurrence of R$^6$ is independently H, $C_1$-$C_6$ alkyl, $C_1$-$C_6$ haloalkyl, $C_1$-$C_6$ hydroxyalkyl, —($C_1$-$C_3$ alkylene)$_m$-($C_3$-$C_7$ cycloalkyl), —($C_1$-$C_3$ alkylene)$_m$-($C_6$-$C_{10}$ aryl), —($C_1$-$C_3$ alkylene)$_m$-(4 to 7-membered heterocycloalkyl), —($C_1$-$C_3$ alkylene)$_m$-(5- or 6-membered monocyclic heteroaryl) or —($C_1$-$C_3$ alkylene)$_m$-(9- or 10-membered bicyclic heteroaryl); and each occurrence of m is independently 0 or 1.

Other embodiments, aspects and features of the present invention are either further described in or will be apparent from the ensuing description, examples, and appended claims.

DETAILED DESCRIPTION OF THE INVENTION

The present invention relates to Substituted Phosphoramidate Compounds and methods of using the Substituted Phosphoramidate Compounds as synthetic intermediates.

Definitions and Abbreviations

The term "$C_1$-$C_6$ alkyl" as used herein, refers to an aliphatic hydrocarbon group, having from 1 to 6 carbon atoms wherein one of its hydrogen atoms is replaced with a bond. A $C_1$-$C_6$ alkyl group may be straight or branched. Non-limiting examples of $C_1$-$C_6$ alkyl groups include methyl, ethyl, n-propyl, isopropyl, n-butyl, sec-butyl, isobutyl, tert-butyl, n-pentyl, neopentyl, isopentyl, n-hexyl, isohexyl and neohexyl. A $C_1$-$C_6$ alkyl group may be unsubstituted or substituted by one or more substituents which may be the same or different, each substituent being independently selected from the group consisting of halo, alkenyl, alkynyl, aryl, cycloalkyl, cyano, hydroxy, —O-alkyl, —O-aryl, -alkylene-O-alkyl, alkylthio, —NH$_2$, —NH(alkyl), —N(alkyl)$_2$, —NH(cycloalkyl), —O—C(O)-alkyl, —O—C(O)-aryl, —O—C(O)-cycloalkyl, —C(O)OH and —C(O)O-alkyl. In one embodiment, a $C_1$-$C_6$ alkyl group is linear. In another embodiment, a $C_1$-$C_6$ alkyl group is branched. Unless otherwise indicated, a $C_1$-$C_6$ alkyl group is unsubstituted.

The term "alkenyl," as used herein, refers to an aliphatic hydrocarbon group containing at least one carbon-carbon double bond and having one of its hydrogen atoms replaced with a bond. An alkenyl group may be straight or branched and contain from about 2 to about 15 carbon atoms. In one embodiment, an alkenyl group contains from about 2 to about 12 carbon atoms. In another embodiment, an alkenyl group contains from about 2 to about 6 carbon atoms. Non-limiting examples of alkenyl groups include ethenyl, propenyl, n-butenyl, 3-methylbut-2-enyl, n-pentenyl, octenyl and decenyl. An alkenyl group may be unsubstituted or substituted by one or more substituents which may be the same or different, each substituent being independently selected from the group consisting of halo, alkenyl, alkynyl, aryl, cycloalkyl, cyano, hydroxy, —O-alkyl, —O-aryl, -alkylene-O-alkyl, alkylthio, —NH$_2$, —NH(alkyl), —N(alkyl)$_2$, —NH(cycloalkyl), —O—C(O)-alkyl, —O—C(O)-aryl, —O—C(O)-cycloalkyl, —C(O)OH and —C(O)O-alkyl. The term "$C_2$-$C_6$ alkenyl" refers to an alkenyl group having from 2 to 6 carbon atoms. Unless otherwise indicated, an alkenyl group is unsubstituted.

The term "alkylene," as used herein, refers to an alkyl group, as defined above, wherein one of the alkyl group's hydrogen atoms has been replaced with a bond. Non-limiting examples of alkylene groups include —CH$_2$—, —CH$_2$CH$_2$—, —CH$_2$CH$_2$CH$_2$—, —CH$_2$CH$_2$CH$_2$CH$_2$—, —CH(CH$_3$)CH$_2$CH$_2$—, —CH(CH$_3$)— and —CH$_2$CH(CH$_3$)CH$_2$—. In one embodiment, an alkylene group has from 1 to about 6 carbon atoms. In another embodiment, an alkylene group is branched. In another embodiment, an alkylene group is linear. In one embodiment, an alkylene group is —CH$_2$—. The term "$C_1$-$C_6$ alkylene" refers to an alkylene group having from 1 to 6 carbon atoms. The term "$C_1$-$C_3$ alkylene" refers to an alkylene group having from 1 to 3 carbon atoms.

The term "$C_6$-$C_{10}$ aryl" refers to phenyl and naphthyl. In one embodiment, an aryl group is phenyl.

The term "cycloalkyl" refers to a non-aromatic monocyclic or multicyclic ring system comprising from about 3 to about 14 ring carbon atoms. The term "3 to 7-membered cycloalkyl" refers to a monocyclic cycloalkyl group having from about 3 to about 7 ring carbon atoms. Examples of "3 to 7-membered cycloalkyl" groups include cyclopropyl, cyclobutyl, cyclopentyl, cyclohexyl and cycloheptyl. The term "7 to 14-membered cycloalkyl" refers to a multicyclic cycloalkyl group having from about 7 to about 14 ring carbon atoms. Examples of "7 to 14-membered cycloalkyl" groups include, but are not limited to adamantyl and octahydro indene. A cycloalkyl group can be optionally substituted with one or more "ring system substituents" which may be the same or different, and are as defined herein below. In one embodiment, a cycloalkyl group is unsubstituted. One or more ring carbon atoms of a cycloalkyl may be functionalized as a carbonyl group. An illustrative example of such a cycloalkyl (also referred to herein as a "cycloalkanoyl" group) includes, but is not limited to, cyclobutanoyl:

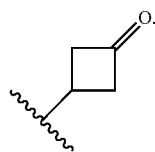

The term "electron-withdrawing group" as used herein, refers to any substituent, that when attached to a carbon atom, draws electron density away from the carbon atom to which it is attached. Non-limiting examples of electron-withdrawing groups include halo, haloalkyl, acyl, carbonyl, carboxyl, ester, —NO$_2$, —CN and —CF$_3$. In one embodiment, an electron withdrawing group is halo. In another embodiment, an electron withdrawing group is F. In another embodiment, an electron withdrawing group is Cl. In another embodiment, an electron withdrawing group is —NO$_2$.

The term "halo" as used herein, refers to fluorine, chlorine, bromine and iodine (alternatively referred to as fluoro, chloro, bromo, and iodo).

The term "5 or 6-membered monocyclic heteroaryl," as used herein, refers to an aromatic monocyclic ring system comprising about 5 to about 6 ring atoms, wherein from 1 to 4 of the ring atoms is independently O, N or S and the remaining ring atoms are carbon atoms. A 5 or 6-membered monocyclic heteroaryl group can be optionally substituted by one or more "ring system substituents" which may be the same or different, and are as defined herein below. A 5 or 6-membered monocyclic heteroaryl group is joined via a ring carbon atom, and any nitrogen atom of a heteroaryl can be optionally oxidized to the corresponding N-oxide. The term "5 or 6-membered monocyclic heteroaryl" also encompasses a 5 or 6-membered monocyclic heteroaryl group, as defined above, which is fused to a benzene ring. Non-limiting examples of 5 or 6-membered monocyclic heteroaryls include pyridyl, pyrazinyl, furanyl, thienyl, pyrimidinyl, pyridone (including N-substituted pyridones), isoxazolyl, isothiazolyl, oxazolyl, oxadiazolyl, thiazolyl, pyrazolyl, furazanyl, pyrrolyl, triazolyl, 1,2,4-thiadiazolyl, pyrazinyl, pyridazinyl, benzofurazanyl, indolyl, azaindolyl, benzimidazolyl, benzothienyl, imidazolyl, benzimidazolyl, thienopyridyl, thienopyrimidyl, pyrrolopyridyl, imidazopyridyl, isoquinolinyl, 1,2,4-triazinyl, benzothiazolyl and the like, and all isomeric forms thereof. Unless otherwise indicated, a 5 or 6-membered monocyclic heteroaryl group is unsubstituted.

The term "9 or 10-membered bicyclic heteroaryl," as used herein, refers to an aromatic bicyclic ring system comprising about 9 to about 10 ring atoms, wherein from 1 to 4 of the ring atoms is independently O, N or S and the remaining ring atoms are carbon atoms. A 9 or 10-membered bicyclic heteroaryl group can be optionally substituted by one or more "ring system substituents" which may be the same or different, and are as defined herein below. A 9 or 10-membered bicyclic heteroaryl group is joined via a ring carbon atom, and any nitrogen atom of a heteroaryl can be optionally oxidized to the corresponding N-oxide. Non-limiting examples of 9 or 10-membered bicyclic heteroaryls include imidazo[1,2-a]pyridinyl, imidazo[2,1-b]thiazolyl, benzofurazanyl, indolyl, azaindolyl, benzimidazolyl, benzothienyl, quinolinyl, benzimidazolyl, quinazolinyl, pyrrolopyridyl, imidazopyridyl, isoquinolinyl, benzoazaindolyl, benzothiazolyl, and the like, and all isomeric forms thereof. Unless otherwise indicated, a 9 or 10-membered bicyclic heteroaryl group is unsubstituted.

The term "heterocycloalkyl," as used herein, refers to a non-aromatic monocyclic or multicyclic ring system comprising 3 to about 11 ring atoms, wherein from 1 to 4 of the ring atoms are independently O, S, N or Si, and the remainder of the ring atoms are carbon atoms. A heterocycloalkyl group can be joined via a ring carbon, ring silicon atom or ring nitrogen atom. In one embodiment, a heterocycloalkyl group is monocyclic and has from about 3 to about 7 ring atoms. In another embodiment, a heterocycloalkyl group is monocyclic has from about 4 to about 7 ring atoms. In another embodiment, a heterocycloalkyl group is bicyclic and has from about 7 to about 11 ring atoms. In still another embodiment, a heterocycloalkyl group is monocyclic and has 5 or 6 ring atoms. In one embodiment, a heterocycloalkyl group is monocyclic. In another embodiment, a heterocycloalkyl group is bicyclic. There are no adjacent oxygen and/or sulfur atoms present in the ring system. Any —NH group in a heterocycloalkyl ring may exist protected such as, for example, as an —N(BOC), —N(Cbz), —N(Tos) group and the like; such protected heterocycloalkyl groups are considered part of this invention. The term "heterocycloalkyl" also encompasses a heterocycloalkyl group, as defined above, which is fused to an aryl (e.g., benzene) or heteroaryl ring. A heterocycloalkyl group can be optionally substituted by one or more "ring system substituents" which may be the same or different, and are as defined herein below. The nitrogen or sulfur atom of the heterocycloalkyl can be optionally oxidized to the corresponding N-oxide, S-oxide or S,S-dioxide. Non-limiting examples of monocyclic heterocycloalkyl rings include oxetanyl, piperidyl, pyrrolidinyl, piperazinyl, morpholinyl, thiomorpholinyl, thiazolidinyl, 1,4-dioxanyl, tetrahydrofuranyl, tetrahydrothiophenyl, delta-lactam, delta-lactone and the like, and all isomers thereof.

A ring carbon atom of a heterocycloalkyl group may be functionalized as a carbonyl group. An illustrative example of such a heterocycloalkyl group is:

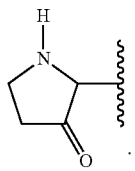

In one embodiment, a heterocycloalkyl group is a 5-membered monocyclic heterocycloalkyl. In another embodiment, a heterocycloalkyl group is a 6-membered monocyclic heterocycloalkyl. The term "3 to 6-membered monocyclic heterocycloalkyl" refers to a monocyclic heterocycloalkyl group having from 3 to 6 ring atoms. The term "4 to 7-membered monocyclic heterocycloalkyl" refers to a monocyclic heterocycloalkyl group having from 4 to 7 ring atoms. The term "7 to 11-membered bicyclic heterocycloalkyl" refers to a bicyclic heterocycloalkyl group having from 7 to 11 ring atoms. Unless otherwise indicated, a heterocycloalkyl group is unsubstituted.

The term "transition metal catalyst," as used herein, refers to a complex comprising a transition metal and one or more ligands, which are independently selected from any organic and/or any inorganic ligands.

Unless expressly stated to the contrary in a particular context, any of the various cyclic rings and ring systems described herein may be attached to the rest of the compound of which they are a part at any ring atom (i.e., any carbon atom or any heteroatom) provided that a stable compound results.

Unless expressly stated to the contrary, all ranges cited above are inclusive; i.e., the range includes the values for the upper and lower limits of the range as well as all values in between.

When any variable occurs more than one time in a compound involved in the process of the invention (e.g., $R^5$ or m), its definition on each occurrence is independent of its definition at every other occurrence. Also, combinations of substituents and/or variables are permissible only if such combinations result in a stable compound.

Unless expressly stated to the contrary, substitution by a named substituent is permitted on any atom in a ring (e.g., cycloalkyl, aryl, or heteroaryl) provided such ring substitution is chemically allowed and results in a stable compound.

In reference to the compounds employed as reactants or reagents in the processes of the invention (e.g., Compounds II, III, and IV), a "stable" compound is one whose structure and properties remain or can be caused to remain essentially unchanged for a period of time sufficient to allow its use in the processes of the invention. In reference to Compound of Formula (I), a "stable" compound is a compound which can be prepared in accordance with the present invention and then isolated and whose structure and properties remain or can be caused to remain essentially unchanged for a period of time sufficient to allow use of the compound for its intended purpose; e.g., for use as a synthetic intermediate to make compounds capable of inhibiting HCV NS5B polymerase, and to make medicinally useful compounds, such as compounds useful for treating HCV infection in a subject.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in Organic Synthesis* (1991), Wiley, New York.

The Substituted Phosphoramidate Compounds can form salts which are also within the scope of this invention. The term "salt(s)", as employed herein, denotes acidic salts formed with inorganic and/or organic acids, as well as basic salts formed with inorganic and/or organic bases. In addition, when a Substituted Phosphoramidate Compound contains both a basic moiety, such as, but not limited to a pyridine or imidazole, and an acidic moiety, such as, but not limited to a carboxylic acid, zwitterions ("inner salts") may be formed and are included within the term "salt(s)" as used herein. In one embodiment, the salt is a pharmaceutically acceptable (i.e., non-toxic, physiologically acceptable) salt. In another embodiment, the salt is other than a pharmaceutically acceptable salt. Salts of the Compounds of Formula (I) may be formed, for example, by reacting a Substituted Phosphoramidate Compound with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use.* (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamine, t-butyl amine, choline, and salts with amino acids such as arginine, lysine and the like. Basic nitrogen-containing groups may be quaternized with agents such as lower alkyl halides (e.g., methyl, ethyl, and butyl chlorides, bromides and iodides), dialkyl sulfates (e.g., dimethyl, diethyl, and dibutyl sulfates), long chain halides (e.g., decyl, lauryl, and stearyl chlorides, bromides and iodides), arylalkyl halides (e.g., benzyl and phenethyl bromides), and others.

All such acid salts and base salts are considered equivalent to the free forms of the corresponding compounds for purposes of the invention. In one embodiment, the acid salts and base salts of the invention are intended to be pharmaceutically acceptable salts within the scope of the invention.

Diastereomeric mixtures can be separated into their individual diastereomers on the basis of their physical chemical differences by methods well-known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Sterochemically pure compounds may also be prepared by using chiral starting materials or by employing salt resolution techniques. Also, some of the Substituted Phosphoramidate Compounds may be atropisomers (e.g., substituted biaryls) and are considered as part of this invention. Enantiomers can also be directly separated using chiral chromatographic techniques, such as chiral HPLC.

It is also possible that the Substituted Phosphoramidate Compounds may exist in different tautomeric forms, and all such stable forms are embraced within the scope of the invention. For example, all stable keto-enol and imine-enamine forms of the compounds are included in the invention.

All stereoisomers (for example, geometric isomers, optical isomers and the like) of the present compounds (including those of the salts, solvates, hydrates and esters of the compounds), such as those which may exist due to the presence of asymmetric carbon or phosphorus atoms, including enantiomeric forms (which may exist even in the absence of asymmetric carbons), rotameric forms, atropisomers, and diastereomeric forms, are contemplated within the scope of this invention. If a Substituted Phosphoramidate Compound incorporates a double bond or a fused ring, both the cis- and trans-forms, as well as mixtures, are embraced within the scope of the invention.

Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974 Recommendations. The use of the terms "salt", "solvate", "ester", and the like, is intended to apply equally to the salt, solvate and ester of enantiomers, diastereomers, rotamers, tautomers or racemates of the inventive compounds.

The following abbreviations are used below and have the following meanings: Ac is acetate, DCM is dichloromethane, Et$_3$N is triethylamine, EtOAc is ethyl acetate, HPLC is high performance liquid chromatography, IPAc is isopropyl acetate, Me is methyl, MTBE is tert-butyl methyl ether, TFA is trifluoroacetic acid, THF is tetrahydrofuran and TLC is thin-layer chromatography.

The Compounds of the Present Invention

In one aspect, the present invention provides Compounds of Formula (I):

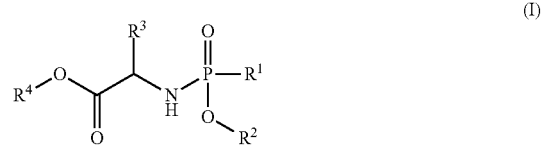

and salts thereof, wherein $R^1$, $R^2$, $R^3$ and $R^4$ are defined above herein.

In one embodiment, the Compound of Formula (I) has the formula (Ia) or (Ib):

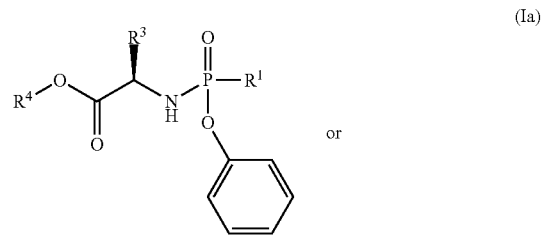

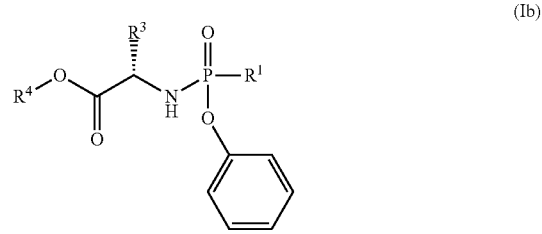

wherein:
$R^1$ is —O—(5 or 6-membered monocyclic heteroaryl) or —S—($C_6$-$C_{10}$ aryl), wherein said 5 or 6-membered monocyclic heteroaryl group or said $C_6$-$C_{10}$ aryl group can be optionally substituted with up to 3 groups, each independently selected from $C_1$-$C_6$ alkyl, —NO$_2$, halo, $C_1$-$C_6$ haloalkyl;
$R^3$ is —$C_1$-$C_6$ alkyl; and
$R^4$ is —$C_1$-$C_6$ alkyl.

In another embodiment, the Compound of Formula (I) has the formula (Ia'), (Ia"), (Ib') or (Ib"):

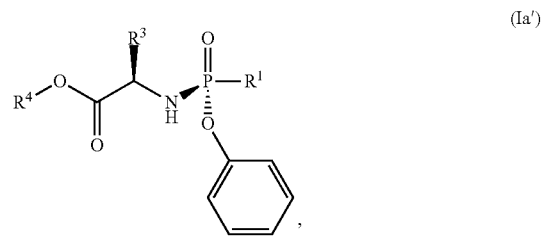

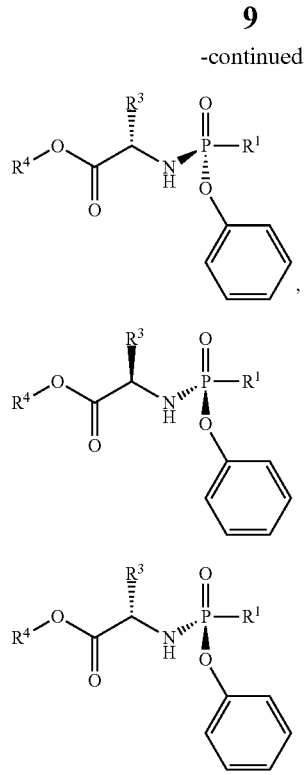

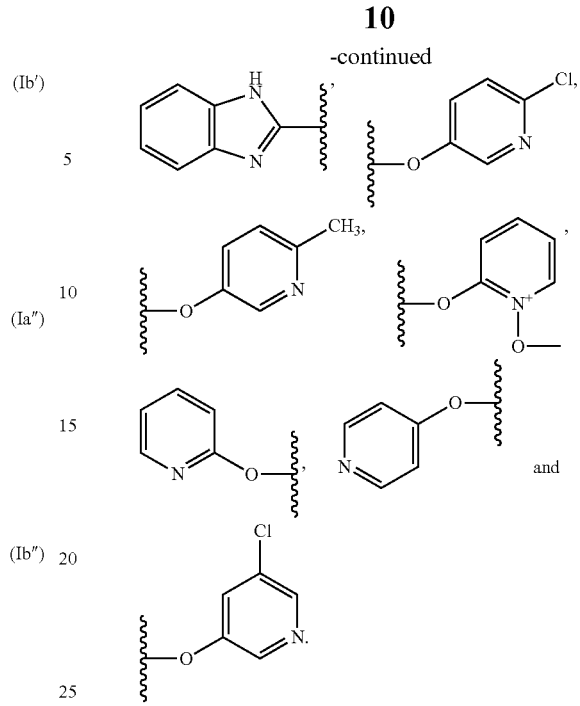

wherein:
R¹ is —O-(5 or 6-membered monocyclic heteroaryl) or —S—($C_6$-$C_{10}$ aryl), wherein said 5 or 6-membered monocyclic heteroaryl group or said $C_6$-$C_{10}$ aryl group can be optionally substituted with up to 3 groups, each independently selected from $C_1$-$C_6$ alkyl, —$NO_2$, halo and $C_1$-$C_6$ haloalkyl;
R³ is —$C_1$-$C_6$ alkyl; and
R⁴ is —$C_1$-$C_6$ alkyl.

In one embodiment, R¹ is —O-(5 or 6-membered monocyclic heteroaryl), which can be optionally substituted with one or more R⁵ groups.

In another embodiment, R¹ is —S—($C_6$-$C_{10}$ aryl), which can be optionally substituted with one or more R⁵ groups.

In another embodiment, R¹ is —O-pyridyl or —S-phenyl, wherein said pyridyl and said phenyl groups can be optionally substituted with up to 3 groups, each independently selected from $C_1$-$C_6$ alkyl, —$NO_2$, halo, $C_1$-$C_6$ haloalkyl.

In still another embodiment, R¹ is —O-pyridyl or —S-phenyl, each of which can be optionally substituted with halo.

In another embodiment, R¹ is selected from:

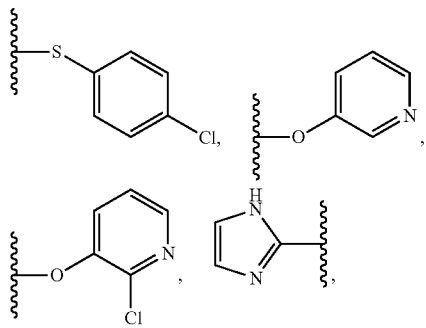

In another embodiment, R¹ is:

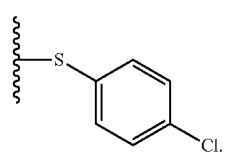 [SMILES: *Sc1ccc(Cl)cc1]

In another embodiment, R¹ is:

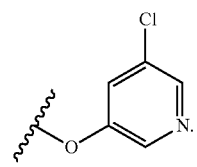 [SMILES: *Oc1cncc(Cl)c1]

In one embodiment, R² is phenyl, which can be optionally substituted with one or more R⁵ groups.
In another embodiment, R² is unsubstituted phenyl.
In one embodiment, R³ is —$C_1$-$C_6$ alkyl.
In another embodiment, R³ is methyl.
In another embodiment, R⁴ is —$C_1$-$C_6$ alkyl.
In another embodiment, R⁴ is isopropyl.
In one embodiment, the Compound of Formula (I) has the structure:

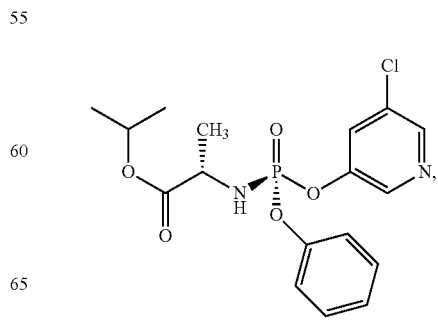

-continued

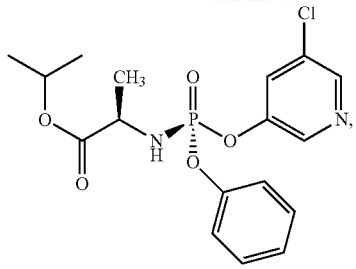

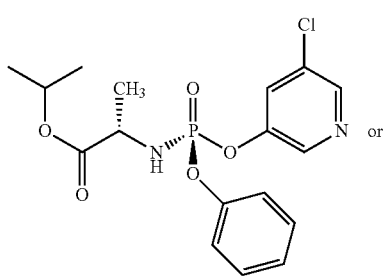

or

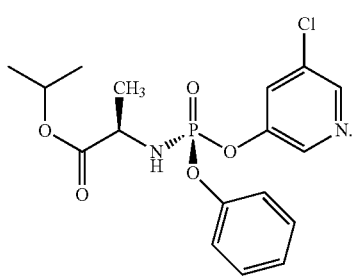

In another embodiment, the Compound of Formula (I) has the structure:

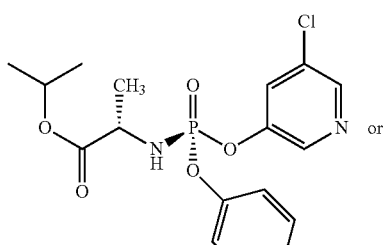

or

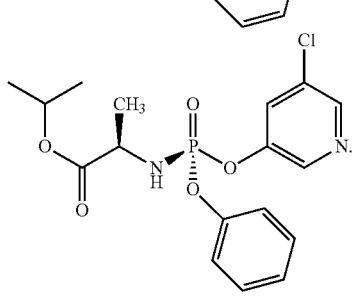

In another embodiment, the Compound of Formula (I) has the structure:

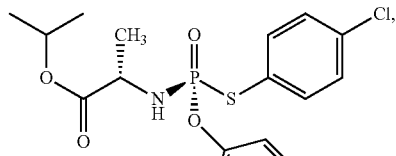

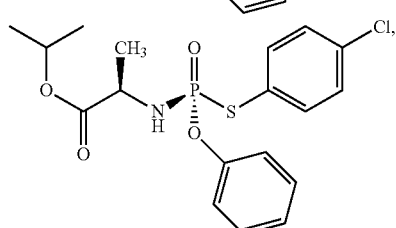

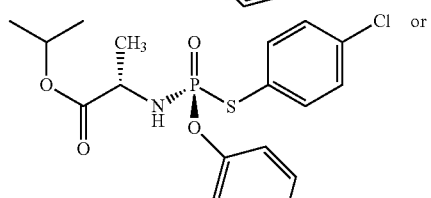

or

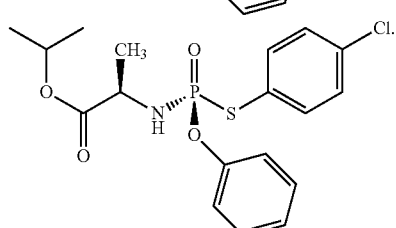
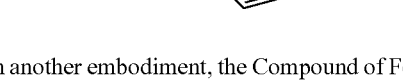

In another embodiment, the Compound of Formula (I) has the structure:

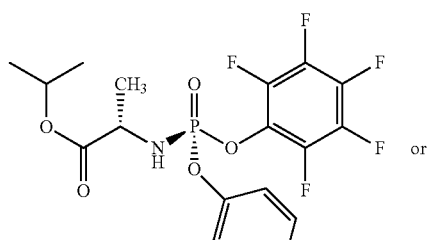

or

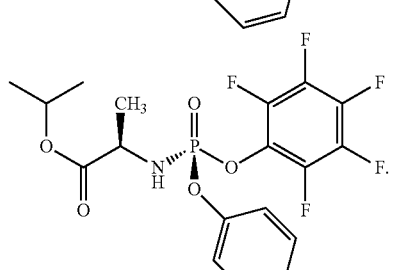

The Processes of the Present Invention

In another aspect, the present invention provides a method (alternately referred to herein as "Process P") for preparing Compounds of Formula (I):

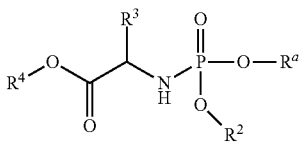
(II)

said method comprising the step of contacting a compound of formula (III):

$$R^a\text{—}OH \quad (III)$$

with a compound of formula (I), in the presence of a base, in an organic solvent A for a time and at a temperature sufficient to form a compound of formula (II), wherein $R^2$, $R^3$ and $R^4$ are as defined above for the compounds of formula (II) and $R^a$—OH is any organic alcohol.

In one embodiment, $R^3$ and $R^4$ are each $C_1$-$C_6$ alkyl.

In another embodiment, $R^3$ is methyl.

In another embodiment, $R^4$ is isopropyl.

In one embodiment, $R^a$ is joined to the compound of formula (II) via a primary carbon atom.

In another embodiment, $R^a$ is joined to the compound of formula (II) via a secondary carbon atom.

In another embodiment, $R^a$ is joined to the compound of formula (II) via a tertiary carbon atom.

In one embodiment, $R^a$ is:

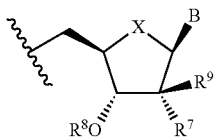

wherein:

X is O, S or $CH_2$;

B is a natural or non-natural purine or pyrimidine base, or B is selected from one of the following groups:

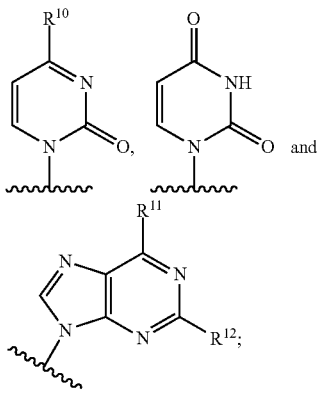

$R^7$ is selected from H, $C_1$-$C_6$ alkyl, $C_2$-$C_6$ alkenyl, $C_2$-$C_6$ alkynyl, halo, —CN, —$N_3$, —$N(R^{13})_2$, $C_1$-$C_6$ haloalkyl, $C_1$-$C_6$ hydroxyalkyl, $C_2$-$C_6$ alkenyl, $C_2$-$C_6$ alkynyl and $C_3$-$C_7$ cycloalkyl;

$R^8$ is selected from H and —C(O)$R^{13}$;

$R^9$ is selected from H, $C_1$-$C_6$ alkyl, $C_2$-$C_6$ alkenyl, $C_2$-$C_6$ alkynyl, halo, —CN, —$N_3$, —$N(R^{13})_2$, $C_1$-$C_6$ haloalkyl, $C_1$-$C_6$ hydroxyalkyl, $C_2$-$C_6$ alkenyl, $C_2$-$C_6$ alkynyl and $C_3$-$C_7$ cycloalkyl;

$R^{10}$, $R^{11}$ and $R^{12}$ are each independently selected from H, $C_1$-$C_6$ alkyl, $C_2$-$C_6$ alkenyl, $C_2$-$C_6$ alkynyl, $C_3$-$C_7$ cycloalkyl, halo, —$OR^{14}$, —$SR^{14}$, —$S(O)R^{14}$, —$S(O)_2R^{14}$, —$S(O)_2N(R^{14})_2$, —NHC(O)$OR^{14}$, —NHC(O)N($R^{14}$)$_2$, $C_1$-$C_6$ haloalkyl, $C_1$-$C_6$ hydroxyalkyl, —O—($C_1$-$C_6$ haloalkyl), —CN, —$NO_2$, —N($R^{14}$)$_2$, —NH($C_1$-$C_6$ alkylene)-(5- or 6-membered monocyclic heteroaryl), —NH($C_1$-$C_6$ alkylene)-(9- or 10-membered bicyclic heteroaryl), —C(O)$R^{14}$, —C(O)$OR^{14}$, —C(O)N($R^{14}$)$_2$ and —NHC(O)$R^{14}$;

each occurrence of $R^{13}$ is independently H or $C_1$-$C_6$ alkyl;

each occurrence of $R^{14}$ is independently selected from H, $C_1$-$C_{10}$ alkyl, $C_1$-$C_6$ haloalkyl, $C_1$-$C_6$ hydroxyalkyl, —($C_1$-$C_3$ alkylene)$_n$-($C_3$-$C_7$ cycloalkyl), —($C_1$-$C_3$ alkylene)$_n$-($C_6$-$C_{10}$ aryl), —($C_1$-$C_3$ alkylene)$_n$-(4 to 7-membered heterocycloalkyl), —($C_1$-$C_3$ alkylene)$_n$-(5- or 6-membered monocyclic heteroaryl) and —($C_1$-$C_3$ alkylene)$_n$-(9- or 10-membered bicyclic heteroaryl); and each occurrence of n is independently 0 or 1.

In one embodiment, X is O; B is a pyrimidine base; $R^9$ is methyl; $R^7$ is selected from F, Cl, —CN, $C_2$-$C_6$ alkynyl, —$NH_2$ and —$N_3$; and $R^8$ is H or —C(O)CH($CH_3$)$_2$.

In another embodiment, $R^9$ is methyl; B is uridine; $R^7$ is selected from F, Cl, $C_2$-$C_6$ alkynyl, and —CN; and $R^8$ is H or —C(O)CH($CH_3$)$_2$.

In another embodiment, $R^9$ is methyl; B is uridine; $R^7$ is —CN and $R^8$ is —C(O)CH($CH_3$)$_2$.

In still another embodiment, $R^9$ is methyl; B is uridine; $R^7$ is —Cl and $R^8$ is —H.

In another embodiment, $R^9$ is methyl; B is uridine; $R^7$ is —F and $R^8$ is —H.

In one embodiment, the organic solvent A is selected from toluene, dichloromethane, benzene, tetrahydrofuran, 2-methyl tetrahydrofuran, ethyl acetate and acetonitrile.

In another embodiment, the organic solvent A is tetrahydrofuran.

In one embodiment, the base employed is selected from: a compound of formula $R^b_2$ Mg, $R^b$MgZ, $R^1$Na, $R^b$K or $R^b$Li, wherein Z is Cl, Br or I; a non-nucleophilic base such as DBU, DBN, tetramethyl guanidine or a phosphazene derived base; an alkali metal hydride, such as LiH, NaH, KH; a metal carbonate of the formula $Li_2CO_3$, $Na_2CO_3$, $K_2CO_3$, and $Cs_2CO_3$ and $MgCO_3$; LDA, LHMDS, NaHMDS, KHMDS, LiOt-Bu, NaOt-Bu, KOt-Bu and TMSOK, wherein each occurrence of $R^b$ is independently selected from $C_1$-$C_6$ alkyl, $C_3$-$C_7$ cycloalkyl and phenyl.

In another embodiment, the base employed is a compound of formula $R^b$MgZ.

In another embodiment, the base employed is a compound of formula $R^b$MgCl.

In another embodiment, the base employed is a compound of formula $R^b$MgCl, wherein $R_b$ is $C_1$-$C_6$ alkyl.

In another embodiment, the base employed is t-butyl-MgCl.

In one embodiment, Process P is conducted at a temperature in a range of from about −40° C. to about 120° C.

In another embodiment, Process P is conducted at a temperature in a range of from about 0° C. to about 100° C.

In another embodiment, Process P is conducted at a temperature in a range of from about 20° C. to about 80° C.

In still another embodiment, Process P is conducted at a temperature in a range of from about 25° C. to about 65° C.

In one embodiment, for Process P, the compound of formula (I) employed has the formula (Ia) or (Ib):

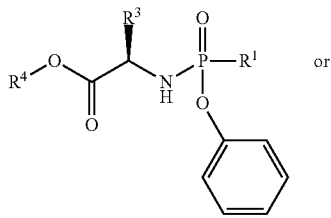
(Ia)

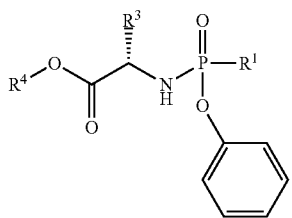
(Ib)

wherein:

R¹ is —O—(5 or 6-membered monocyclic heteroaryl) or —S—(C₆-C₁₀ aryl), wherein said 5 or 6-membered monocyclic heteroaryl group or said C₆-C₁₀ aryl group can be optionally substituted with up to 3 groups, each independently selected from C₁-C₆ alkyl, —NO₂, halo, C₁-C₆ haloalkyl;

R³ is —C₁-C₆ alkyl; and

R⁴ is —C₁-C₆ alkyl.

In another embodiment, for Process P, the compound of formula (I) employed has the formula (Ia'), (Ia"), (Ib') or (Ib"):

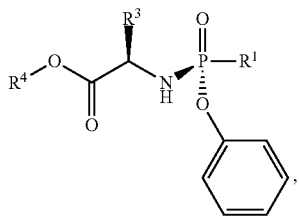
(Ia')

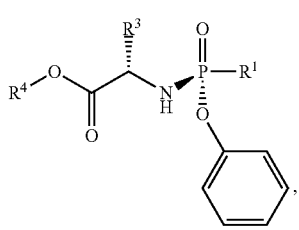
(Ib')

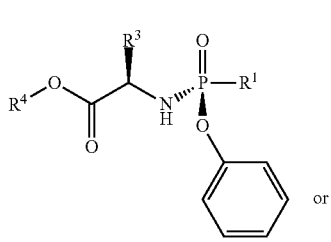
(Ia")
or

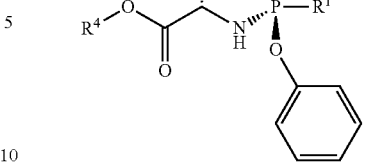
(Ib")

wherein:

R¹ is —O-(5 or 6-membered monocyclic heteroaryl) or —S—(C₆-C₁₀ aryl), wherein said 5 or 6-membered monocyclic heteroaryl group or said C₆-C₁₀ aryl group can be optionally substituted with up to 3 groups, each independently selected from C₁-C₆ alkyl, —NO₂, halo, C₁-C₆ haloalkyl;

R³ is —C₁-C₆ alkyl; and

R⁴ is —C₁-C₆ alkyl.

In another embodiment, for Process P, the compound of formula (I) employed has the structure:

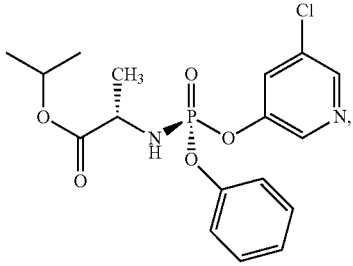

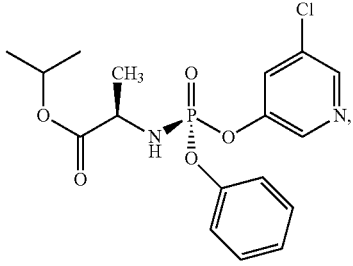

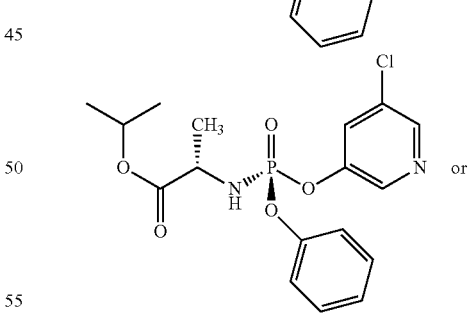
or

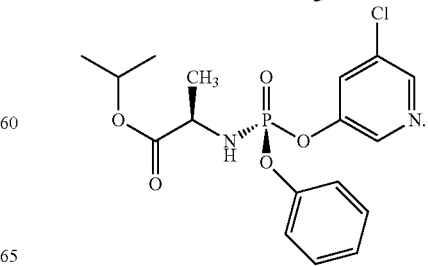

In another embodiment, for Process P, the compound of formula (I) employed has the structure:

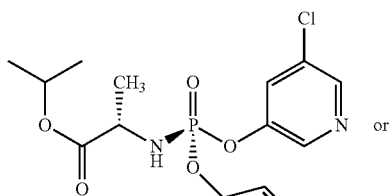

or

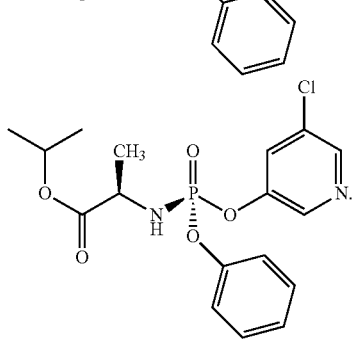

In another embodiment, for Process P, the compound of formula (I) employed has the structure:

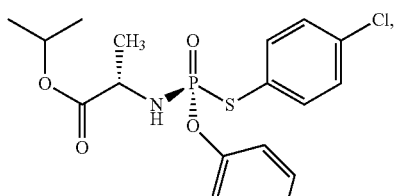

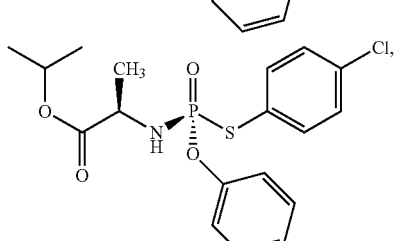

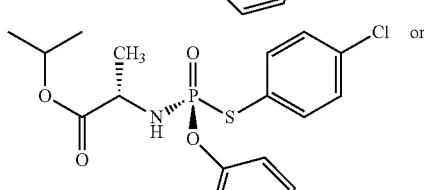

or

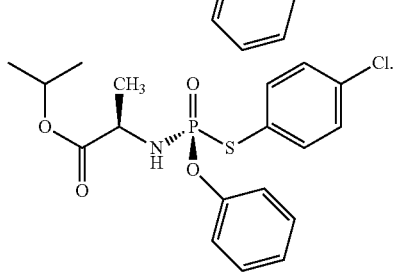

In one embodiment, for Process P:
the organic solvent A is THF;
the base employed is a compound of formula $R^bMgZ$; and
the process is conducted at a temperature in a range of from about 0° C. to about 100° C.

In another embodiment, for Process P:
the organic solvent A is THF;
the base employed is a compound of formula $R^bMgZ$;
the process is conducted at a temperature in a range of from about 0° C. to about 100° C.; and
the compound of formula (I) employed has the formula (Ia) or (Ib):

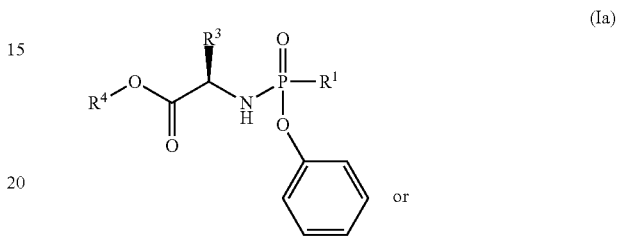

or

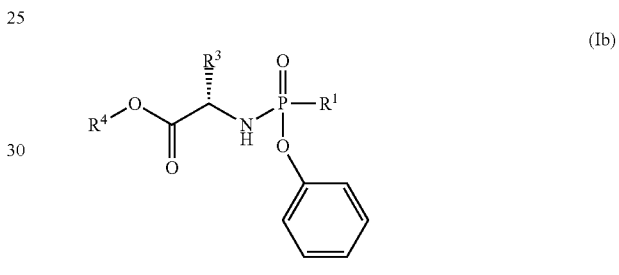

wherein:
$R^1$ is —O-(5 or 6-membered monocyclic heteroaryl) or —S—($C_6$-$C_{10}$ aryl), wherein said 5 or 6-membered monocyclic heteroaryl group or said $C_6$-$C_{10}$ aryl group can be optionally substituted with up to 3 groups, each independently selected from $C_1$-$C_6$ alkyl, —$NO_2$, halo, $C_1$-$C_6$ haloalkyl;
$R^3$ is —$C_1$-$C_6$ alkyl; and
$R^4$ is —$C_1$-$C_6$ alkyl.

In another embodiment, for Process P:
the organic solvent A is THF;
the base employed is a compound of formula $R^bMgCl$, wherein $R^b$ is $C_1$-$C_6$ alkyl;
the process is conducted at a temperature in a range of from about 20° C. to about 80° C.; and
the compound of formula (I) employed has the formula (Ia) or (Ib):

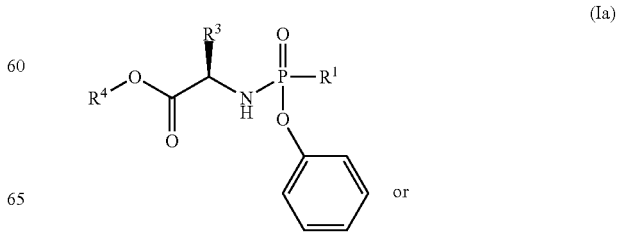

or

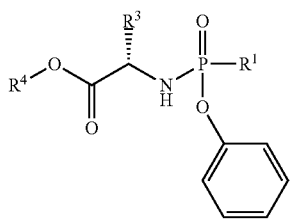
(Ib)

wherein:

R$^1$ is —O-(5 or 6-membered monocyclic heteroaryl) or —S—(C$_6$-C$_{10}$ aryl), wherein said 5 or 6-membered monocyclic heteroaryl group or said C$_6$-C$_{10}$ aryl group can be optionally substituted with up to 3 groups, each independently selected from C$_1$-C$_6$ alkyl, —NO$_2$, halo, C$_1$-C$_6$ haloalkyl;

R$^3$ is —C$_1$-C$_6$ alkyl; and

R$^4$ is —C$_1$-C$_6$ alkyl.

In still another embodiment, for Process P:

the organic solvent A is THF;

the base employed is a compound of formula t-butylMgCl;

the process is conducted at a temperature in a range of from about 25° C. to about 65° C.; and the compound of formula (I) employed has the formula (Ia'), (Ia''), (Ib') or (Ib''):

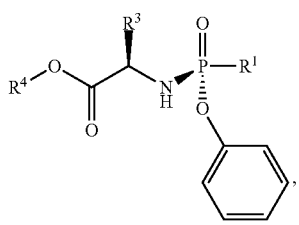
(Ia')

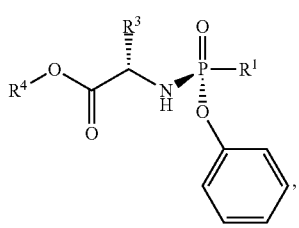
(Ib')

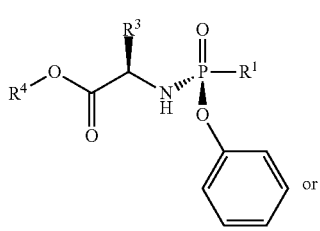
(Ia'')

or

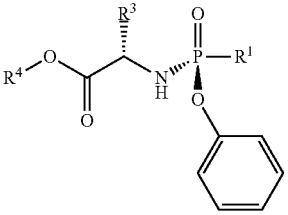
(Ib'')

wherein:

R$^1$ is —O-(5 or 6-membered monocyclic heteroaryl) or —S—(C$_6$-C$_{10}$ aryl), wherein said 5 or 6-membered monocyclic heteroaryl group or said C$_6$-C$_{10}$ aryl group can be optionally substituted with up to 3 groups, each independently selected from C$_1$-C$_6$ alkyl, —NO$_2$, halo, C$_1$-C$_6$ haloalkyl;

R$^3$ is —C$_1$-C$_6$ alkyl; and

R$^4$ is —C$_1$-C$_6$ alkyl.

In one embodiment, Process P can be conducted in any organic solvent.

In one aspect, the present invention provides a method ("Process A") for preparing a Compound of Formula (IV):

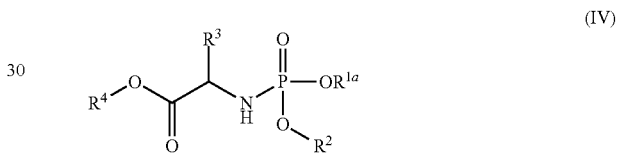
(IV)

said method comprising the step of contacting a compound of formula (V):

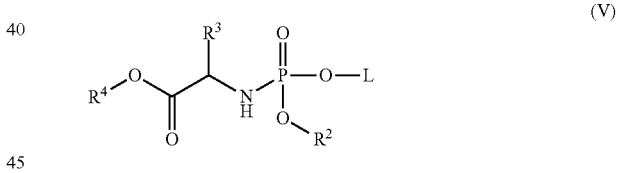
(V)

with a compound of formula (VI):

(VI)

in the presence of a non-nucleophilic base, in an organic solvent B for a time and at a temperature sufficient to form a compound of formula (IV), wherein:

L is a phenyl group or 6-membered heteroaryl group, wherein said phenyl group and said 6-membered heteroaryl group is substituted on a ring carbon atom with at least one electron-withdrawing substituent group;

R$^{1a}$ is selected from 5 or 6-membered monocyclic heteroaryl and 9 or 10-membered bicyclic heteroaryl, wherein said 5 or 6-membered monocyclic heteroaryl group and said 9 or 10-membered bicyclic heteroaryl groups, can each be optionally substituted with one or more R$^5$ groups;

R$^2$ is C$_6$-C$_{10}$ aryl;

R$^3$ is —C$_1$-C$_6$ alkyl;

R$^4$ is —C$_1$-C$_6$ alkyl;

each occurrence of R$^5$ is independently selected from —C$_1$-C$_6$ alkyl, halo, —OR$^6$, —C(O)R$^6$, —CO$_2$R$^6$, —SR$^6$, —$C_1$-$C_6$ hydroxyalkyl, —$C_1$-$C_6$ haloalkyl, —$N(R^6)_2$, —$S(O)R^6$, —$S(O)_2R^6$, —CN and —$NO_2$;

each occurrence of $R^6$ is independently H, $C_1$-$C_6$ alkyl, $C_1$-$C_6$ haloalkyl, $C_1$-$C_6$ hydroxyalkyl, —($C_1$-$C_3$ alkylene)$_m$-($C_3$-$C_7$ cycloalkyl), —($C_1$-$C_3$ alkylene)$_m$-($C_6$-$C_{10}$ aryl), —($C_1$-$C_3$ alkylene)$_m$-(4 to 7-membered heterocycloalkyl), —($C_1$-$C_3$ alkylene)$_m$-(5- or 6-membered monocyclic heteroaryl) or —($C_1$-$C_3$ alkylene)$_m$-(9- or 10-membered bicyclic heteroaryl); and each occurrence of m is independently 0 or 1.

In one embodiment, for Process A, $R^2$ is phenyl.

In another embodiment, for Process A, $R^3$ is methyl.

In another embodiment, for Process A, $R^4$ is isopropyl.

In one embodiment, for Process A, L is a phenyl group substituted with at least one halo group.

In another embodiment, for Process A, L is a phenyl group substituted with at least one nitro group.

In another embodiment, for Process A, L is a 6-membered heteroaryl group substituted with at least one halo group.

In still another embodiment, for Process A, L is a 6-membered heteroaryl group substituted with at least one nitro group.

In another embodiment, for Process A, L is a pyridyl group substituted with at least one halo group.

In one embodiment, for Process A, L is pentafluorophenyl.

In another embodiment, for Process A, L is p-nitrophenyl.

In one embodiment, for Process A, organic solvent B is selected from toluene, dichloromethane, benzene, tetrahydrofuran, 2-methyl tetrahydrofuran, ethyl acetate and acetonitrile.

In another embodiment, for Process A, organic solvent B is tetrahydrofuran.

In one embodiment, for Process A, the non-nucleophilic base employed is an organic amine base such as DBU, DBN, tetramethyl guanidine or a phosphazene derived base; or an alkali metal alkoxide, such as LiOt-Bu, NaOt-Bu or KOt-Bu.

In another embodiment, for Process A, the non-nucleophilic base employed is an organic amine base.

In another embodiment, for Process A, the non-nucleophilic base employed is an alkali metal alkoxide base.

In still another embodiment, for Process A, the non-nucleophilic base employed is LiOt-Bu.

In another embodiment, for Process A, the non-nucleophilic base employed is DIPEA.

In one embodiment, Process A is conducted at a temperature range of from about −50° C. to about 70° C.

In another embodiment, Process A is conducted at a temperature range of from about −40° C. to about 50° C.

In another embodiment, Process A is conducted at a temperature range of from about −20° C. to about 30° C.

In another embodiment, Process A is conducted at a temperature range of from about −10° C. to about 25° C.

In still another embodiment, Process A is conducted at a temperature range of from about 0° C. to about 20° C.

In another embodiment, Process A is conducted at a temperature of about −40° C.

In another embodiment, Process A is conducted at a temperature of about 0° C.

In one embodiment, for Process A, the non-nucleophilic base employed is LiOt-Bu and Process A is conducted at a temperature of about 0° C.

In another embodiment, for Process A, the non-nucleophilic base employed is DIPEA and Process A is conducted at a temperature of about −40° C.

In one embodiment, for Process A, the compound of formula (IV) that is made by Process A has a diastereomeric ratio of about 20:1.

In one embodiment, for Process A, the compound of formula (IV) that is made by Process A has a diastereomeric ratio of about 30:1.

In one embodiment, for Process A, the compound of formula (IV) that is made by Process A has a diastereomeric ratio of about 40:1.

In one embodiment, for Process A, the compound of formula (IV) that is made by Process A has a diastereomeric ratio of about 50:1.

In one embodiment, for Process A, the compound of formula (IV) that is made by Process A has a diastereomeric ratio of about 60:1.

In one embodiment, for Process A, the compound of formula (IV) that is made by Process A has a diastereomeric ratio of about 70:1.

In one embodiment, for Process A, the compound of formula (IV) that is made by Process A has a diastereomeric ratio of about 80:1.

In one embodiment, for Process A, the compound of formula (IV) that is made by Process A has a diastereomeric ratio of about 90:1.

In one embodiment, for Process A, the compound of formula (IV) that is made by Process A has a diastereomeric ratio of about 95:1.

In one embodiment, for Process A, the compound of formula (IV) that is made by Process A has a diastereomeric ratio of about 98:1.

In one embodiment, for Process A, the compound of formula (IV) that is made by Process A has a diastereomeric ratio of about 99:1.

In one embodiment, for Process A, the compound of formula (IV) made by Process A has the formula (IVa), (IVb), (IVc) or (IVd):

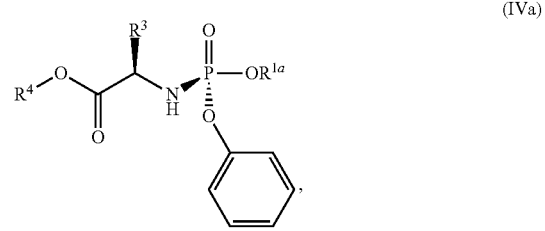

(IVa)

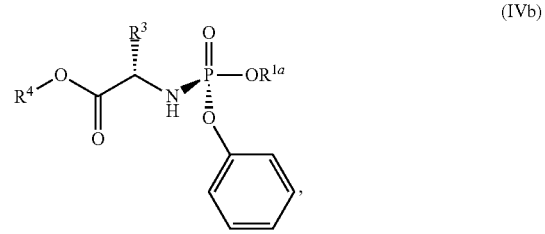

(IVb)

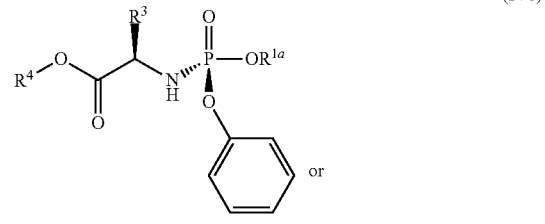

(IVc)

or (IVd)

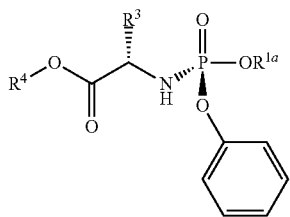

wherein:

$R^{1a}$ is -(6-membered monocyclic heteroaryl), wherein said 6-membered monocyclic heteroaryl group can be optionally substituted with up to 3 groups, each independently selected from $C_1$-$C_6$ alkyl, —$NO_2$, halo and $C_1$-$C_6$ haloalkyl;

$R^3$ is —$C_1$-$C_6$ alkyl; and $R^4$ is —$C_1$-$C_6$ alkyl.

In one embodiment, the compound of formula (IV) made by Process A has the structure:

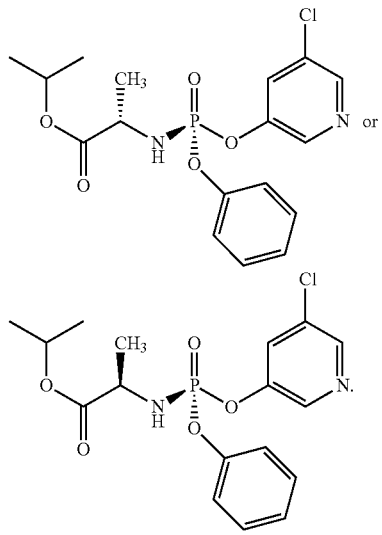

In another embodiment, the compound of formula (IV) made by Process A has the structure:

In one embodiment, Process A can be conducted in any organic solvent.

EXAMPLES

General Methods

Solvents, reagents, and intermediates that are commercially available were used as received. Reagents and intermediates that are not commercially available were prepared in the manner as described below. $^1$H NMR spectra were obtained on a Bruker Ultrashield 400 (400 MHz) and are reported as ppm downfield from $Me_4Si$ with number of protons, multiplicities, and coupling constants in Hertz indicated parenthetically. Where LC/MS data are presented, analyses was performed using an Agilent 1100 LCMS system with LC column: Ascentis Express C18, 2.7 micron, 150 mm×3 mm ID; gradient flow: 0 minutes—10% $CH_3CN$/2 mM aqueous $NH_4COOH$/HCOOH, 6 minutes—95% $CH_3CN$, 6-12 minutes—95% $CH_3CN$, 14 minutes—stop. The observed parent ion is given. Flash column chromatography was performed using pre-packed normal phase silica from Biotage, Inc. or bulk silica from Fisher Scientific. Unless otherwise indicated, column chromatography was performed using a gradient elution of hexanes/ethyl acetate, from 100% hexanes to 100% ethyl acetate.

Example 1

General Preparation of Compounds of Formula (I)

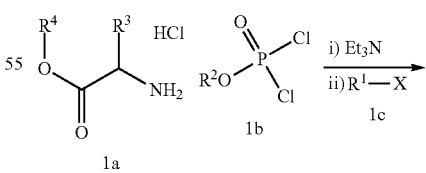

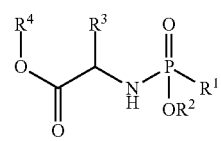

(I)

A compound of formula 1a (19.22 g, 115 mmol) is charged to an inerted overhead stirred jacketed vessel followed by a suitable organic solvent (100-200 mL) to provide a solution which is then cooled to about −20° C. A solution of a compound of formula 1b (25.0 g, 1.0 eq.) in a suitable organic solvent (100-200 mL) is then added while maintaining internal temperature below −10° C. and the resulting solution is then cooled back to −20° C. To the cooled solution is added a suitable base (3.2 eq.) over 60 minutes with further cooling to control the resulting exotherm and maintain the internal reaction temperature below −17° C. The resulting reaction was re-cooled to −20° C. and allowed to stand at this temperature without stirring for 30 minutes. A solution of compound 1c (1.0 eq) in a suitable organic solvent (100-200 mL) is then added to the reaction over a period of 75 minutes and the resulting reaction is allowed to age at −20° C. until the reaction has progressed to a suitable point. The reaction mixture is then warmed to room temperature and the resulting slurry is filtered. The collected solid is then washed with THF (2×100 mL) and the filtrates are combined to provide a solution of a compound of formula (I) (typically 80-90% yield). The Compounds of Formula (I) so obtained can then be further purified using workup, crystallization or chromatography methods well-known to those skilled in the art of organic synthesis.

General Workup Procedure for Compounds of Formula (I)

A solution of a compound of formula (I), obtained using the method described above, is diluted with MTBE (or other organic non water miscible solvents such as EtOAc and IPAc), then washed sequentially with an aqueous hydrochloric acid (2×), aqueous sodium hydrogencarbonate (2×), then water. The organic phase can then be concentrated in vacuo to provide a compound of formula (I).

General Crystallization Method for Purifying Compounds of Formula (I)

On concentration several products 1d form solids. These can be crystallized by those skilled in the art typically involving a solubilizing organic solvent such as MTBE, EtOAc, IPAc and an anti-solvent typically hexane or heptane. Often one isomer of the products 1d is less soluble than others and the solid product which can be isolated using filtration is enhanced in this less soluble isomer giving a purity upgrade.

Purification of Compounds of Formula (I) Using Chromatography

Pure single stereoisomers of the compounds of formula (I) can be isolated using chromatographic techniques well-known to those skilled in the art of organic synthesis, such as thin-layer chromatography, flash column chromatography on silica gel, MPLC or HPLC.

Example 2

Preparation of Compound 1

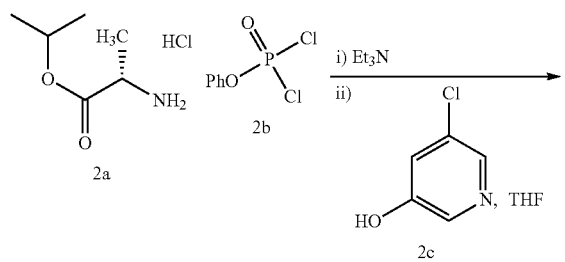

-continued

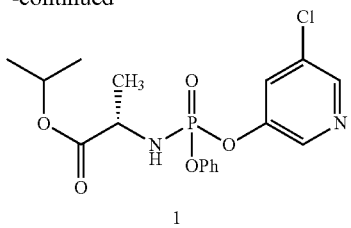

1

Compound 2a hydrochloride salt (19.22 g, 115 mmol) was charged to an inerted overhead stirred jacketed vessel. To the vessel was then added THF (125 mL) and the resulting solution was cooled to −20° C. A solution of compound 2b (25.0 g, 114 mmol) in THF (125 mL) was then added to the compound 2a solution, while maintaining the internal reaction temperature below −10° C. during the course of the addition. The resulting solution was then cooled to −20° C. and triethylamine (51.2 mL, 367 mmol) was added over a 60 minute period with further cooling employed to control the resulting exotherm and maintain the internal reaction temperature below −17° C. during the course of the addition. The resulting reaction was then cooled to −20° C. and allowed to age for 30 minutes at this temperature. A solution of compound 2c (114 mmol) in THF (150 mL) was then added to the reaction over a 75 minute period and resulting reaction was allowed to age at −20° C. until monitoring via HPLC indicated >98% consumption of the starting materials. The reaction mixture was then warmed to room temperature and the resulting slurry was filtered to remove triethylamine hydrochloride. The resulting filter cake was washed with THF (2×100 mL) and the filtrates were combined to provide a solution of compound 1 as a mixture of diastereomers (80% yield).

Example 3

Procedure for Purifying Compound 1 Via Crystallization

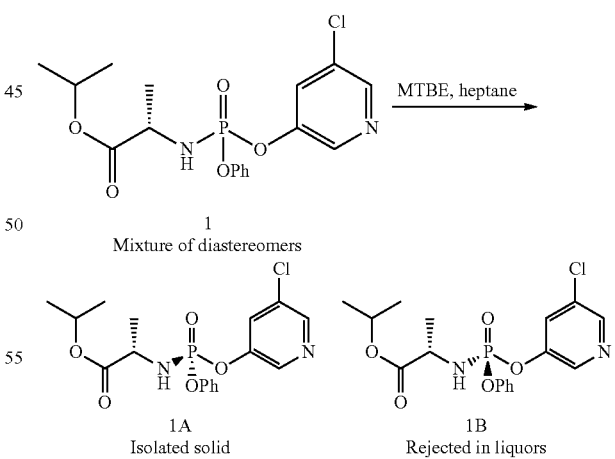

A solution of compound 1 (obtained using the method described in Example 2) was concentrated in vacuo. The resulting residue was triturated with a mixture of MTBE in heptane (10 mL/g) and agitated until a thick slurry was formed. Filtration of the slurry provided compound 1A as a white solid >98:2 dr (30-35%). Compound 1B was isolated directly from the liquors.

Compound 1A $^1$H NMR (400 MHz, CDCl3): δ 8.45-8.40 (m, 2H), 7.71-7.68 (m, 1H), 7.40-7.32 (m, 2H), 7.27-7.18 (m, 3H), 5.0286 (heptet, J=6.3 Hz, 1H), 4.17-4.06 (m, 1H), 4.01-3.86 (m, 1H), 1.42 (d, J=7.0 Hz, 3H), 1.25 (d, J=5.86 Hz, 3H), 1.24 (d, 5.87 Hz, 3H).

$^{13}$C NMR (100 MHz, CDCl$_3$): δ 172.45 (d, J=9.1 Hz), 150.20 (d, J=6.8 Hz), 147.56 (d, J=6.8 Hz), 145.19, 140.23 (d, J=6.1 Hz), 131.96, 129.90, 127.84 (d, J=4.6 Hz), 125.55, 120.11 (d, J=4.6 Hz), 69.65, 50.60 (d, J=1.6 Hz), 21.64 (d, J=6.9 Hz), 21.03 (d, J=3.8 Hz).

$^{31}$P NMR (162 MHz, CDCl$_3$): δ −2.261 (+ trace at −24.128)

Compound 1B $^1$H NMR (400 MHz, CDCl3): δ 7.36-7.30 (m, 2H), 7.26-7.21 (m, 2H), 7.18-7.13 (m, 1H), 5.04 (heptet, J=6.26 Hz, 1H), 4.81-4.69 (m, 1H), 4.01-3.90 (m, 1H), 3.53 (t, J=10.17 Hz, 1H), 1.37 (d, J=7.04 Hz, 3H), 1.35 (d, J=6.26 Hz, 3H), 1.33 (d, J=6.26 Hz, 3H), 1.26 (d, J=6.26 Hz, 3H), 1.25 (d, J=6.26 Hz, 3H).

$^{13}$C NMR (100 MHz, CDCl$_3$): δ 173.052 (d, J=7.6 Hz), 151.000 (d, J=6.9 Hz), 129.574, 124.636, 120.217 (d, J=5.3 Hz), 72.380 (d, J=5.3 Hz), 69.119, 50.359, 23.728 (d, J=7.6), 23.683 (d, J=7.6 Hz), 21.717, 21.640, 21.107 (d, J=4.6 Hz).

$^{31}$P NMR (162 MHz, CDCl$_3$): δ 1.3449.

Example 4

Procedure for Purifying Compound 2 Via Crystallization

MTBE in heptane (10 mL/g) and agitated until a thick slurry was formed. Filtration of the slurry provided compound 2A as a white solid>99:1 dr (30-35%). Compound 2B was isolated directly from the liquors.

Compound 2A $^1$H NMR (500 MHz, CDCl3): δ 8.45-8.40 (m, 2H), 7.71-7.68 (m, 1H), 7.40-7.32 (m, 2H), 7.27-7.18 (m, 3H), 5.02 (heptet, J=5.7 Hz, 1H), 4.17-4.06 (m, 1H), 4.01-3.86 (m, 1H), 1.41 (d, J=6.7 Hz, 3H), 1.24 (d, J=5.4 Hz, 3H), 1.23 (d, 5.4 Hz, 3H).

$^{13}$C NMR (125 MHz, CDCl$_3$): δ 172.45 (d, J=8.0 Hz), 150.20 (d, J=6.3 Hz), 147.56 (d, J=6.3 Hz), 145.18, 140.23 (d, J=5.8 Hz), 131.95, 129.90, 127.84 (d, J=4.3 Hz), 125.54, 120.11 (d, J=4.3 Hz), 69.65, 50.60 (d, J=1.3 Hz), 21.63 (d, J=6.3 Hz), 21.02 (d, J=3.2 Hz).

$^{31}$P NMR (202 MHz, CDCl$_3$): δ −2.41

Compound 2B $^1$H NMR (400 MHz, CDCl3): δ 7.36-7.30 (m, 2H), 7.26-7.21 (m, 2H), 7.18-7.13 (m, 1H), 5.037 (heptet, J=6.26 Hz, 1H), 4.81-4.69 (m, 1H), 4.01-3.90 (m, 1H), 3.5309 (t, J=10.17 Hz, 1H), 1.3742 (d, J=7.04 Hz, 3H), 1.35175 (d, J=6.26 Hz, 3H), 1.33025 (d, J=6.26 Hz, 3H), 1.25885 (d, J=6.26 Hz, 3H), 1.253 (d, J=6.26 Hz, 3H).

$^{13}$C NMR (100 MHz, CDCl$_3$): δ 173.0.52 (d, J=7.6 Hz), 151.000 (d, J=6.9 Hz), 129.574, 124.636, 120.217 (d, J=5.3 Hz), 72.380 (d, J=5.3 Hz), 69.119, 50.359, 23.728 (d, J=7.6), 23.683 (d, J=7.6 Hz), 21.717, 21.640, 21.107 (d, J=4.6 Hz).

$^{31}$P NMR (162 MHz, CDCl$_3$): δ 1.3449.

Example 5

Alternate Procedure for Purifying Compound 1 Via Crystallization

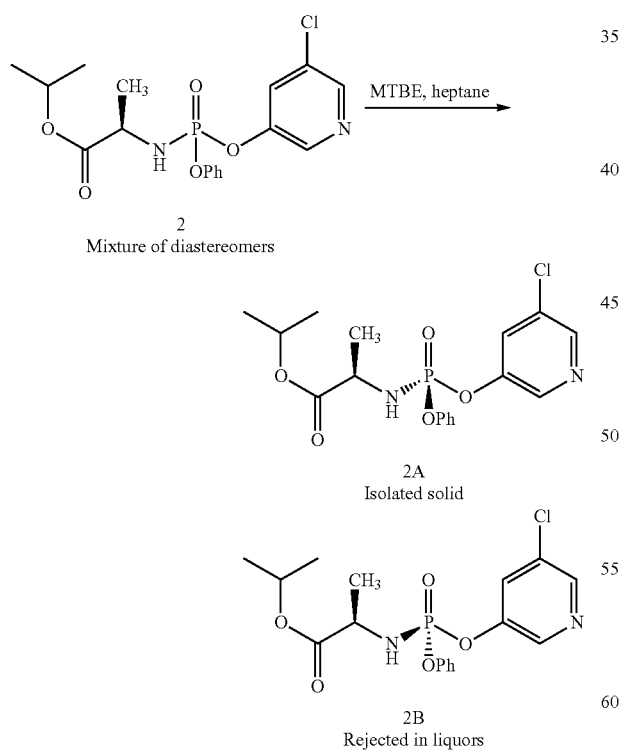

A solution of compound 2 (obtained using the method described in Example 2 and substituting the enantiomer of compound 2a in place of compound 2a) was concentrated in vacuo. The resulting residue was triturated with a mixture of A solution of compound 1 was concentrated in vacuo. The resulting residue was dissolved in MTBE (2 mL/g) and heated to 40° C. n-heptane (10 mL/g) was then added over 3 hours with seeding after ~2 mL/g heptane was added. A thick slurry resulted, which was then cooled to room temperature. Subsequent filtration of the slurry provided compound 1A as a white solid in greater than >98:2 dr (~35% isolated yield).

Example 6

Procedure for Making Compounds 3A and 3B

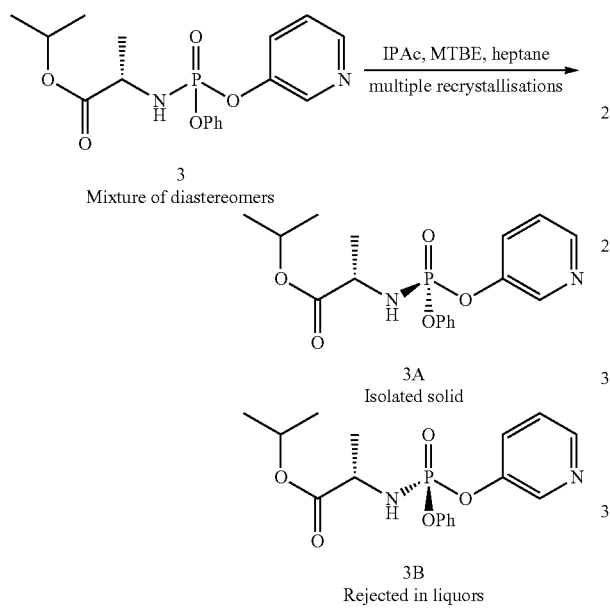

Trituration of compound 3 (made using the method described in Example 2 and substituting 4-hydroxy pyridine for compound 2c) with a mixture of IPAc, MTBE and heptane provided a slurry with the solid enhanced in diastereomer 3A. Following isolation and recrystallisations from IPAc-heptane, compound 3A was isolated in 96.2:3.8 dr

Example 7

Alternate Procedure for Purifying Compound 1 Via Crystallization

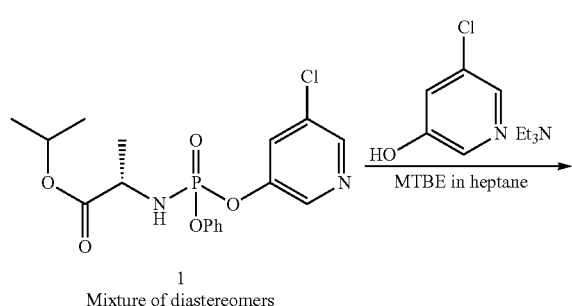

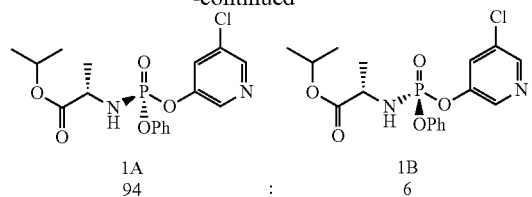

Compound 1 was added to a mixture of 5% MTBE in heptane (10 mL/g), forming a slurry. Addition of 0.1 equiv 5-chloro-3-hydroxypyridine and 1 equiv triethylamine to the slurry allowing the resulting mixture to age at room temperature for 4 days provided a 94:6 mixture of 1A:1B. Addition of aqueous HCl and IPAc forms a biphasic mixture. The organic layer was washed with aqueous HCl, aqueous sodium hydrogen carbonate and then water. Solvent switching the organic layer into a 5% IPAc in heptane mixture (10 volumes) and filtration provided 1A in >99.5:0.5 dr.

Example 8

Procedure for Coupling Compound 1A with a Secondary Alcohol

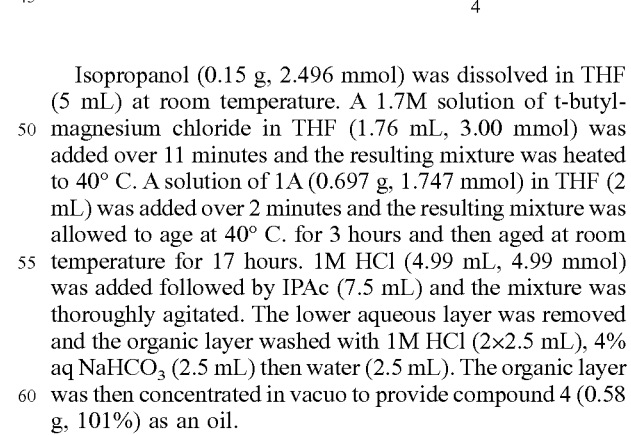

Isopropanol (0.15 g, 2.496 mmol) was dissolved in THF (5 mL) at room temperature. A 1.7M solution of t-butyl-magnesium chloride in THF (1.76 mL, 3.00 mmol) was added over 11 minutes and the resulting mixture was heated to 40° C. A solution of 1A (0.697 g, 1.747 mmol) in THF (2 mL) was added over 2 minutes and the resulting mixture was allowed to age at 40° C. for 3 hours and then aged at room temperature for 17 hours. 1M HCl (4.99 mL, 4.99 mmol) was added followed by IPAc (7.5 mL) and the mixture was thoroughly agitated. The lower aqueous layer was removed and the organic layer washed with 1M HCl (2×2.5 mL), 4% aq NaHCO$_3$ (2.5 mL) then water (2.5 mL). The organic layer was then concentrated in vacuo to provide compound 4 (0.58 g, 101%) as an oil.

$^1$H NMR (400 MHz, CDCl3): δ 7.36-7.30 (m, 2H), 7.26-7.21 (m, 2H), 7.18-7.13 (m, 1H), 5.04 (heptet, J=6.26 Hz, 1H), 4.81-4.69 (m, 1H), 4.01-3.90 (m, 1H), 3.58-3.46 (m, 1H), 1.37 (d, J=7.04 Hz, 3H), 1.35 (d, J=6.26 Hz, 3H), 1.33 (d, J=6.26 Hz, 3H), 1.26 (d, J=6.26 Hz, 3H), 1.25 (d, J=6.26 Hz, 3H).

$^{13}$C NMR (100 MHz, CDCl$_3$): δ 173.052 (d, J=7.6 Hz), 151.000 (d, J=6.9 Hz), 129.574, 124.636, 120.217 (d, J=5.3 Hz), 72.380 (d, J=5.3 Hz), 69.119, 50.359, 23.728 (d, J=7.6), 23.683 (d, J=7.6 Hz), 21.717, 21.640, 21.107 (d, J=4.6 Hz).
$^{31}$P NMR (162 MHz, CDCl$_3$): δ 1.3449.
MS: 330 (M+H)

Example 9

Preparation of Compound 5

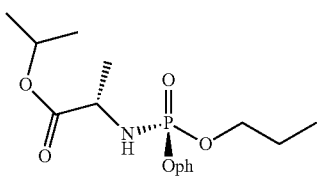

Compound 5 was made in 94% yield using the method described in Example 8 and substituting n-propanol in place of isopropanol.

$^1$H NMR (400 MHz, CDCl3): δ 7.35-7.29 (m, 2H), 7.25-7.21 (m, 2H), 7.18-7.12 (m, 1H), 5.03 (heptet, J=6.26 Hz), 4.10-4.02 (m, 2H), 4.00-3.91 (m, 1H), 3.59-3.50 (m, 1H), 1.76-1.64 (m, 2H), 1.37 (d, J=7.04 Hz, 3H), 1.25 (d, J=6.26 Hz, 3H), 1.25 (d, J=6.26 Hz, 3H), 0.94 (t, J=7.04 Hz, 3H).
$^{13}$C NMR (100 MHz, CDCl$_3$): δ 173.052 (d, J=7.7 Hz), 150.932 (d, J=6.9 Hz), 129.596, 124.705, 120.186 (d, J=4.6 Hz), 69.134, 68.692 (d, J=6.2 Hz), 50.306, 21.694, 21.633, 21.077 (d, J=4.7 Hz), 10.020.
$^{31}$P NMR (162 MHz, CDCl$_3$): 2.4132.

Example 10

Procedure for Coupling Compound 1A with a Nucleoside

Compound 10a (1.22 mmol) was dissolved in anhydrous THF (5 mL). To the resulting solution was added t-butyl-magnesium chloride (1.7M solution in THF, 2.15 mL, 3.66 mmol) over a period of 30 minutes and the resulting solution was allowed to age for 15 minutes at room temperature. The reaction mixture was then heated to 40° C. and a solution of compound 1A (0.68 g, 1.708 mmol) in THF (1.5 mL) was added over a period of 30 minutes and the resulting solution was allowed to age for 24 hours at 40° C. (>98% conversion by LCAP at 210 nm). The resulting reaction was then cooled to room temperature and aqueous HCl (1M, 7.31 mL, 7.31 mmol) and IPAc (7.5 mL) were added to provide a biphasic mixture. The organic layer was collected and washed sequentially with 1M HCl (2×2.5 mL), 4% aqueous sodium hydrogen carbonate (2×2.5 mL) and water (2.5 mL).

The washed organic layer was then (assay 88-94%) was then solvent switched into IPAc (5 mL/g), the resulting solution was heated to 40° C. and compound 6 was crystallized using slow addition of heptane (10 mL/g) and seeding during the heptane addition.

Example 11

Preparation of Compound 6

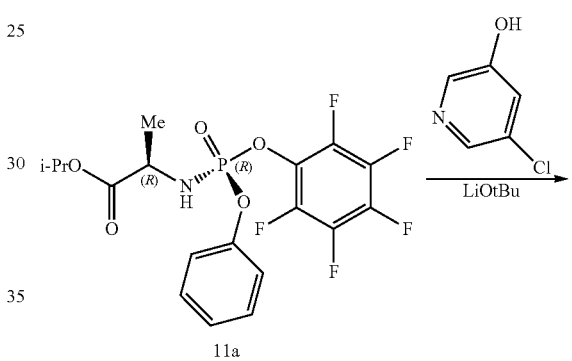

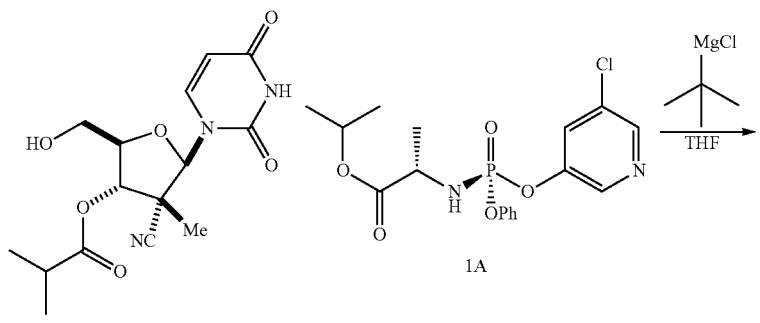

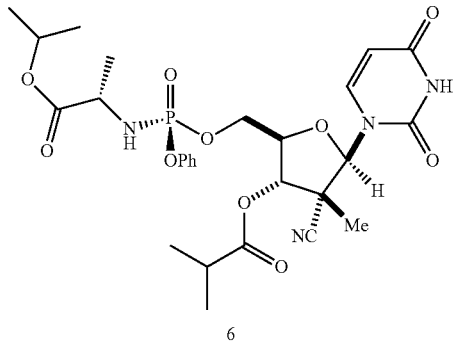

-continued

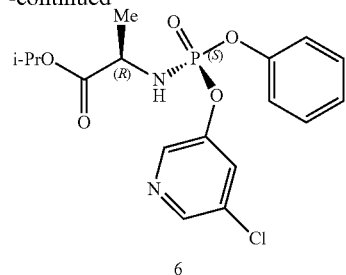

6

To a 0° C. solution of 5-chloro-3-hydroxypyridine (3.00 g, 23.16 mmol) in tetrahydrofuran (90 mL) was added lithium tert-butoxide (1.0 M in THF, 23.16 ml, 23.16 mmol) dropwise, so as to maintain the internal reaction temperature below 10° C.

In a separate flask, compound 11a (12.07 g, 26.6 mmol) was dissolved in tetrahydrofuran (60.0 mL). This solution was then added dropwise to the lithium phenoxide solution over a 5 minute period while maintaining the internal reaction temperature below 10° C. The mixture was aged at 0-10° C. for 2 hours, then 0.5M aqueous citric acid (90 mL) and MTBE (90 mL) were added. The resulting mixture was agitated, and the organic phase was collected and washed with 200 g/L brine (90 mL), dried over MgSO$_4$, filtered, concentrated in vacuo, and purified using silica gel chromatography (0:100 to 50:50 EtOAc:Hexanes) to provide 6 (8.92 g, 22.4 mmol, 97% yield). $^1$H-NMR δ (ppm)(DMSO-d$_6$): 1.11 (6 H, dd, J=6.3, 3.3 Hz), 1.20 (3 H, d, J=7.1 Hz), 3.89-3.97 (1 H, m), 4.79-4.84 (1 H, m), 6.71 (1 H, dd, J=14.2, 10.1 Hz), 7.24 (1 H, t, J=7.4 Hz), 7.29 (2 H, d, J=8.1 Hz), 7.42 (2 H, t, 7.8 Hz), 7.86 (1 H, d, J=2.0 Hz), 8.47 (1 H, s), 8.53 (1 H, d, J=2.1 Hz).

Example 12

Preparation of Compound 7

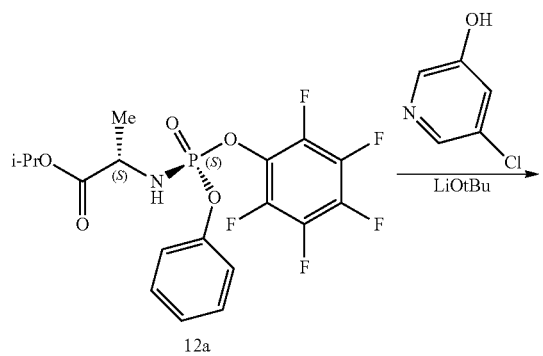

12a

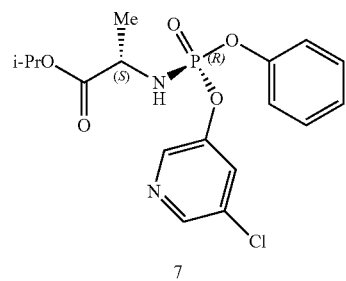

7

To a 0° C. solution of 5-chloro-3-hydroxypyridine (3.00 g, 23.16 mmol) in tetrahydrofuran (90 mL) was added lithium tert-butoxide (1.0 M in THF, 23.16 ml, 23.16 mmol) dropwise, so as to maintain the internal reaction temperature below 10° C.

In a separate flask, compound 12a (10.0 g, 22.1 mmol) was dissolved in tetrahydrofuran (50.0 mL). This solution was added dropwise to the lithium phenoxide solution over 2 min below 10° C. The cooling bath was then removed. This solution was then added dropwise to the lithium phenoxide solution over a 5 minute period while maintaining the internal reaction temperature below 10° C. The mixture was aged at 0-10° C. for 2 hours, then 0.5M aqueous citric acid (150 mL) and MTBE (100 mL) were added. The organics were dried over MgSO$_4$, filtered, concentrated in vacuo, and purified using silica gel chromatography (0:100 to 70:30 EtOAc:Hexanes) to provide compound 7 (8.1 g, 22.4 mmol, 92% yield). $^1$H-NMR δ (ppm)(DMSO-d$_6$): 1.11 (6 H, dd, J=6.3, 3.3 Hz), 1.20 (3 H, d, J=7.1 Hz), 3.89-3.97 (1 H, m), 4.79-4.84 (1 H, m), 6.71 (1 H, dd, J=14.2, 10.1 Hz), 7.24 (1 H, t, J=7.4 Hz), 7.29 (2 H, d, J=8.1 Hz), 7.42 (2 H, t, 7.8 Hz), 7.86 (1 H, d, J=2.0 Hz), 8.47 (1 H, s), 8.53 (1 H, d, J=2.1 Hz).

Example 13

Alternate Preparation of Compound

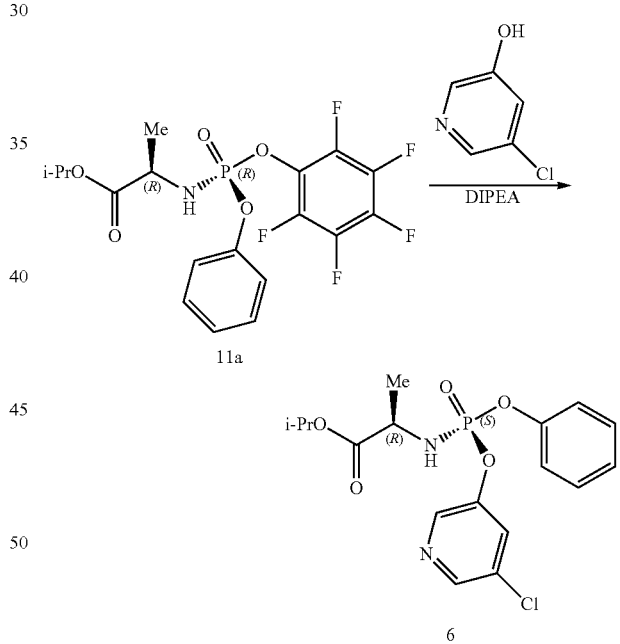

6

To a −40° C. solution of 5-chloro-3-hydroxypyridine (7.5 kg) and diisopropylethylamine (19.4 kg) in tetrahydrofuran (77 kg) was added a solution of compound 11a (17.1 kg) in tetrahydrofuran (112 kg) dropwise over 2 hours, maintaining the internal temperature between −47° C. and −39° C. The mixture was aged at this temperature for 57 hours. The mixture was then added to a 0-5° C. solution of citric acid monohydrate (36.0 kg) in water (170 kg) dropwise over 1.5 hours. MTBE (127 kg) was then added, and the aqueous phase was removed. The organic phase was dried over MgSO$_4$ (94 kg) for 5 hours, then filtered. The filter cake was washed with MTBE (2×51 kg). The combined organics were concentrated in vacuo by vacuum distillation to below 55 L with the portionwise addition of 130 kg MTBE. The solution was then diluted with MTBE (203 kg) and washed with a 10% aqueous K$_3$PO$_4$ solution (2×175 kg) followed by water (40 kg) followed by 10% aqueous K$_3$PO$_4$ (170 kg) followed by water (80 kg, 80 kg, 100 kg, 100 kg, 100 kg). The organic phase was dried over MgSO$_4$ (85 kg) for 2 hours, then filtered. The filter cake was washed with MTBE (2×50 kg). The organics were concentrated in vacuo by vacuum distillation to approximately 14 L, then transferred to a drum with the aid of MTBE (10.0 kg) to provide a solution of compound 6 (24.4 kg, 45.6 wt %). The compound 6 solution (22.6 kg) was concentrated in vacuo by vacuum distillation to between 18 and 21 L, then cooled to between −5 and 5° C. n-Heptane (14 kg) was added, followed by seed crystals of compound 6 (0.050 kg). The mixture was maintained at −5 to 0° C. for 3 hours, after which n-heptane (63 kg) was added over 3 hours. The mixture was aged between −5 and 15° C. for 14 hours, cooled to at −5 to 0° C. The suspended solids were collected by filtration and washed with a mixture of MTBE (0.7 kg) and n-heptane (6.3 kg). The solids remaining in the vessel were suspended in a mixture of MTBE (3.6 kg) and n-heptane (35 kg) at −5 to 0° C., and the filtered solids were added. The mixture was aged at 5 to 0° C. for 2 hours, after which the solids were collected by filtration. The cake wash washed with a mixture of MTBE (0.8 kg) and n-heptane (7.2 kg) then dried to provide compound 6 (8.6 kg, 57% yield). $^1$H-NMR δ (ppm)(DMSO-d$_6$): 1.11 (6 H, dd, J=6.3, 3.3 Hz), 1.20 (3 H, d, J=7.1 Hz), 3.89-3.97 (1 H, m), 4.79-4.84 (1 H, m), 6.71 (1 H, dd, J=14.2, 10.1 Hz), 7.24 (1 H, t, J=7.4 Hz), 7.29 (2 H, d, J=8.1 Hz), 7.42 (2 H, t, 7.8 Hz), 7.86 (1 H, d, J=2.0 Hz), 8.47 (1H, s), 8.53 (1 H, d, J=2.1 Hz); MS (ESI) m/z: 399.1 [M+H]$^+$.

Example 14

Alternate Preparation of Compound 7

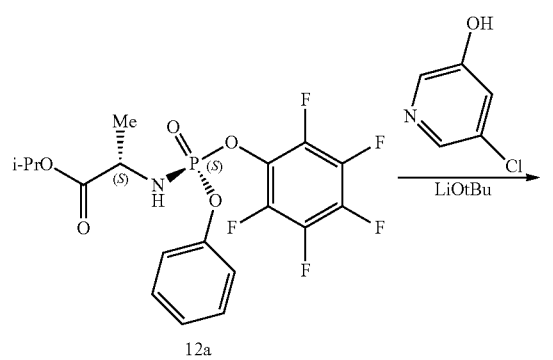

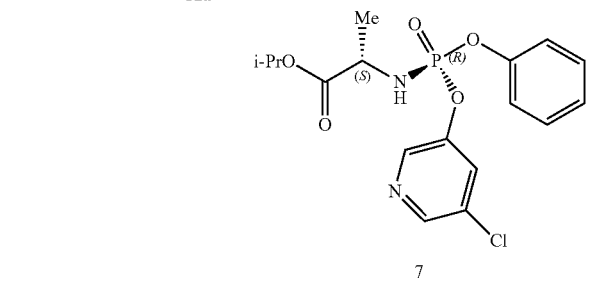

To a −40° C. solution of 5-chloro-3-hydroxypyridine (7.5 kg) and diisopropylethylamine (19.6 kg) in tetrahydrofuran (76 kg) was added a solution of compound 12a (17.0 kg) in tetrahydrofuran (93 kg) dropwise over 2.5 hours, maintaining the internal temperature between −45° C. and −35° C. The mixture was aged at this temperature for 50 hours. The mixture was then added to a −5 to 5° C. solution of citric acid monohydrate (37.0 kg) in water (170 kg) dropwise over 3 hours. MTBE (203 kg) and water (150 kg) were then added, and the aqueous phase was removed. The organic phase was dried over MgSO$_4$ (100 kg) for 1 hour, then filtered. The filter cake was washed with MTBE (2×50 kg). The combined organics were concentrated in vacuo by vacuum distillation to between 17 and 34 L with the portionwise addition of 126 kg MTBE. The solution was then diluted with MTBE (204 kg) and washed with a 10% aqueous K$_3$PO$_4$ solution (170 kg, 173 kg) followed by water (42 kg) followed by 10% aqueous K$_3$PO$_4$ (178 kg) followed by water (68 kg, 68 kg, 82 kg, 77 kg, 62 kg). The organic phase was dried over MgSO$_4$ (50 kg) for 2 hours, then filtered. The filter cake was washed with MTBE (2×50 kg).

The organics were concentrated in vacuo by vacuum distillation to approximately 14 L, then transferred to a drum with the aid of MTBE (19.0 kg) to provide a solution of compound 3b (33.6 kg, 31.6 wt %). The compound 3b solution (33.6 kg) was concentrated in vacuo by vacuum distillation to between 18 and 21 L, then cooled to between −5 and 5° C. n-Heptane (7.2 kg) was added, followed by seed crystals of compound 3b (0.032 kg). The mixture was maintained at −5 to 0° C. for 1 hour, after which n-heptane (65 kg) was added over 2 hours. The mixture was aged between −5 and 15° C. for 18 hours, cooled to at −5 to 0° C. The suspended solids were collected by filtration and washed with a mixture of MTBE (02.2 kg) and n-heptane (20 kg), then dried to provide compound 3b (8.5 kg, 57% yield). $^1$H-NMR δ (ppm)(DMSO-d$_6$): 1.11 (6 H, dd, J=6.3, 3.3 Hz), 1.20 (3 H, d, J=7.1 Hz), 3.89-3.97 (1 H, m), 4.79-4.84 (1 H, m), 6.71 (1 H, dd, J=14.2, 10.1 Hz), 7.24 (1 H, t, J=7.4 Hz), 7.29 (2 H, d, J=8.1 Hz), 7.42 (2 H, t, 7.8 Hz), 7.86 (1 H, d, J=2.0 Hz), 8.47 (1 H, s), 8.53 (1 H, d, J=2.1 Hz); MS (ESI) m/z: 399.1 [M+H]$^+$.

While the foregoing specification teaches the principles of the present invention, with examples provided for the purpose of illustration, the practice of the invention encompasses all of the usual variations, adaptations and/or modifications that come within the scope of the following claims. All publications, patents and patent applications cited herein are incorporated by reference in their entirety into the disclosure.

The invention claimed is:

1. A compound having the formula:

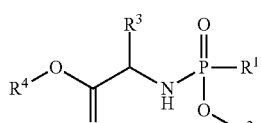

or a salt thereof, wherein:

R$^1$ is selected from:

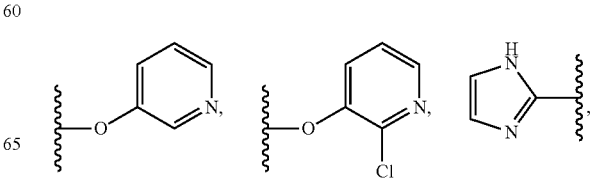

-continued

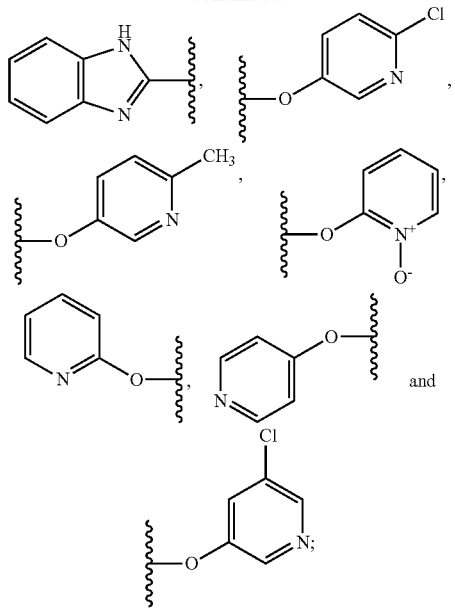

R² is selected from C6-C10 aryl, 5 or 6-membered monocyclic heteroaryl and 9 or 10-membered bicyclic heteroaryl, wherein said C6-C10 aryl group, said 5 or 6-membered monocyclic heteroaryl group and said 9 or 10-membered bicyclic heteroaryl group can be optionally substituted with one or more R⁵ groups;

R³ is selected from C1-C6 alkyl, C3-C7 cycloalkyl, phenyl or benzyl, wherein said C3-C7 cycloalkyl group, said phenyl group and the phenyl moiety of said benzyl group can be optionally substituted with one or more R⁵ groups;

R⁴ is selected from C1-C6 alkyl, C2-C6 alkenyl, —(C1-C3 alkylene)$_m$-(C3-C14 cycloalkyl) and —(C1-C3 alkylene)$_m$-(C6-C10 aryl);

each occurrence of R⁵ is independently selected from —C1-C6 alkyl, halo, —OR⁶, —C(O)R⁶, —CO2R⁶, —SR⁶, —C1-C6 hydroxyalkyl, —C1-C6 haloalkyl, —N(R⁶)2, —S(O)R⁶, —S(O)₂R⁶, —CN and —NO2;

each occurrence of R⁶ is independently H, C1-C6 alkyl, C1-C6 haloalkyl, C1-C6 hydroxyalkyl, —(C1-C3 alkylene)$_m$-(C3-C7 cycloalkyl), —(C1-C3 alkylene)$_m$-(C6-C10 aryl), —(C1-C3alkylene)$_m$-(4 to 7-membered heterocycloalkyl), —(C1-C3 alkylene)$_m$-(5- or 6-membered monocyclic heteroaryl) or —(C1-C3 alkylene)$_m$-(9- or 10-embered bicyclic heteroaryl); and each occurrence of m is independently 0 or 1.

2. The compound of claim 1, wherein R² is phenyl, which can be optionally substituted with one or more R⁵ groups.

3. The compound of claim 1, wherein R³ is —C1-C6 alkyl.

4. The compound of claim 1, having the formula:

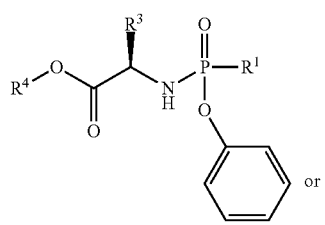

(Ia)

or

-continued

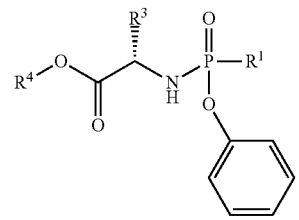

(Ib)

wherein:
R³ is —C1-C6 alkyl; and
R⁴ is —C1-C6 alkyl.

5. The compound of claim 4, having the formula:

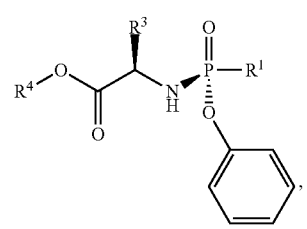

(Ia')

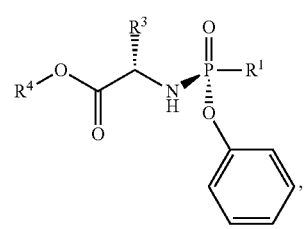

(Ib')

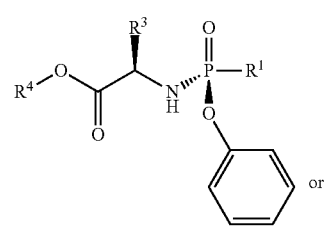

(Ia")

or

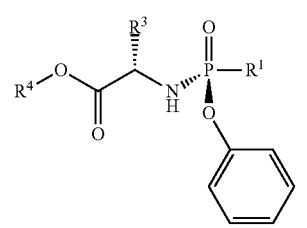

(Ib")

wherein:
R³ is —C1-C6 alkyl; and
R⁴ is —C1-C 06 alkyl.

6. The compound of claim 1, wherein R¹ is selected from:

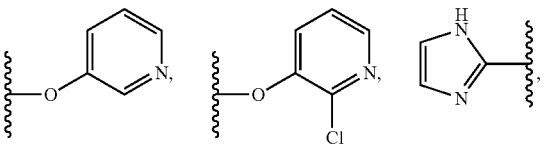

-continued
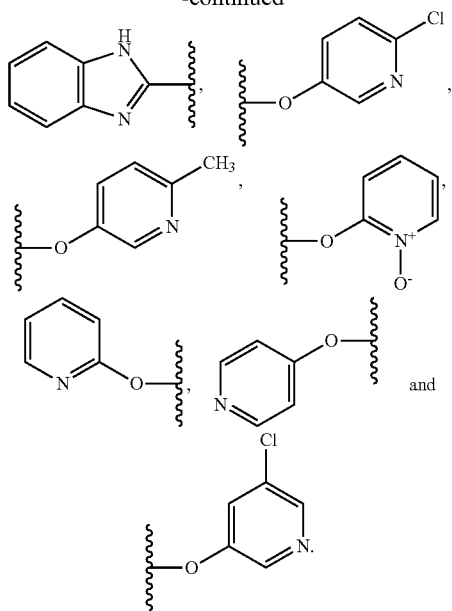
7. The compound of claim 1, wherein R³ is methyl.
8. The compound of claim 1 having the structure:
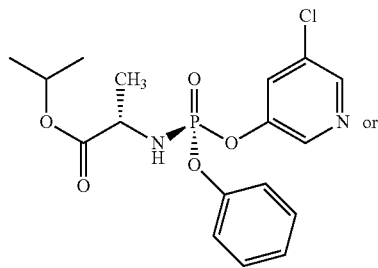 or
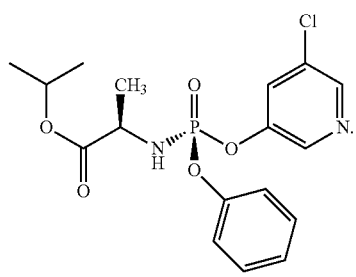
* * * * *